US012616619B2

(12) United States Patent　(10) Patent No.: US 12,616,619 B2
Liu et al.　(45) Date of Patent: May 5, 2026

(54) NONWOVEN AND ABSORBENT ARTICLES CONTAINING THE SAME

(71) Applicant: The Procter & Gamble Company, Cincinnati, OH (US)

(72) Inventors: Zhe Liu, Beijing (CN); Jiahui Wang, Beijing (CN); Lifeng Zhao, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 895 days.

(21) Appl. No.: 17/511,869

(22) Filed: Oct. 27, 2021

(65) Prior Publication Data

US 2022/0133554 A1　May 5, 2022

Related U.S. Application Data

(63) Continuation of application No. PCT/CN2020/125265, filed on Oct. 30, 2020.

(51) Int. Cl.
*A61F 13/534*　(2006.01)
*A61F 13/15*　(2006.01)
(Continued)

(52) U.S. Cl.
CPC .. *A61F 13/534* (2013.01); *A61F 2013/15959* (2013.01); *A61F 2013/51019* (2013.01); *A61F 2013/53062* (2013.01)

(58) Field of Classification Search
CPC .......... A61F 13/534; A61F 2013/15959; A61F 2013/51019; A61F 2013/53062;
(Continued)

(56) References Cited

U.S. PATENT DOCUMENTS 4,323,069 A * 4/1982 Ahr ........................ A61F 13/512
428/137
5,713,884 A * 2/1998 Osborn, III ........... A61F 13/476
604/385.24
(Continued)

FOREIGN PATENT DOCUMENTS

CN　106109103 A　11/2016
CN　109415858 A　3/2019
(Continued)

OTHER PUBLICATIONS

Jun Jia, Donggang Yao, Youjiang Wang, Manufacturing Ultra Fine Filaments by Cold Air Attenuation, 2010, ASME 2010 International Manufacturing Science and Engineering Conference (Year: 2010).*
(Continued)

*Primary Examiner* — Rebecca E Eisenberg
*Assistant Examiner* — Brandon W. Levy
(74) *Attorney, Agent, or Firm* — Gregory P. Habiak; Christian M. Best

(57) ABSTRACT

The present disclosure relates to an absorbent article comprising a liquid pervious topsheet, a liquid impervious backsheet, an absorbent core disposed between the topsheet and the backsheet, and an intermediate layer disposed between the topsheet and the absorbent core, wherein the intermediate layer comprises a nonwoven which comprises a plurality of apertures, absorbent fibers, and ultrafine fibers. The nonwoven comprises the ultrafine fibers of about 3% to about 35% by weight of the nonwoven, and at least most of the plurality of apertures have a hydraulic diameter in the range of about 600 μm to about 4500 μm.

18 Claims, 12 Drawing Sheets

(51) Int. Cl.
*A61F 13/51* (2006.01)
*A61F 13/53* (2006.01)

(58) Field of Classification Search
CPC ...... A61F 2013/15983; A61F 13/53747; A61F
13/53708; A61F 2013/53782; A61F
13/53713; A61F 2013/53721; A61F
2013/15487; A61F 2013/530868; A61F
2013/530897; A61F 2013/51002; A61F
2013/51011; A61F 2013/5103; A61F
2013/51085; A61F 2013/51052; A61F
13/51; A61F 13/512; A61F 13/15203;
A61F 13/53; B32B 5/266; B32B
2262/0253; B32B 2262/04; B32B
2262/124; B32B 2307/724; B32B 3/266;
B32B 5/022; B32B 5/271; B32B
2262/0261; B32B 2262/0284; B32B
2262/144; B32B 2307/718; B32B
2307/726; B32B 5/02; B32B 2307/7265;
B32B 2555/02; D04H 1/425; D04H
1/4258; D04H 1/4334; D04H 1/435;
D04H 1/43838; D04H 1/492; D04H
1/43825; Y10T 428/24273; Y10T
442/659; B29C 2793/0045
See application file for complete search history.

(56) References Cited

U.S. PATENT DOCUMENTS

| | | | | |
|---|---|---|---|---|
| 5,783,503 A | * | 7/1998 | Gillespie | .................. D04H 3/16 |
| | | | | 428/394 |
| 5,833,678 A | * | 11/1998 | Ashton | ................ A61F 13/534 |
| | | | | 604/366 |
| 5,885,267 A | * | 3/1999 | Mishima | ........... A61F 13/51305 |
| | | | | 604/378 |
| 6,103,953 A | * | 8/2000 | Cree | ................. A61F 13/47218 |
| | | | | 604/366 |
| 6,608,236 B1 | | 8/2003 | Burnes et al. | |
| 7,956,236 B2 | | 6/2011 | Ponomarenko et al. | |
| 9,554,950 B2 | | 1/2017 | Seyler | |
| 2007/0073254 A1 | * | 3/2007 | Ponomarenko | ....... A61F 13/512 |
| | | | | 604/383 |
| 2016/0235604 A1 | * | 8/2016 | Ehrnsperger | ............ A61F 13/53 |
| 2016/0287450 A1 | * | 10/2016 | Andersson | ................ B32B 5/26 |

FOREIGN PATENT DOCUMENTS

| | | | |
|---|---|---|---|
| EP | 0747029 A1 | * | 12/1996 |
| EP | 0804915 A1 | * | 11/1997 |
| EP | 2356961 A1 | | 8/2011 |
| EP | 3205318 A1 | | 8/2017 |
| JP | H102191758 A | | 7/1990 |
| JP | 2018104846 A | | 7/2018 |
| WO | 9311726 A1 | | 6/1993 |
| WO | 9851250 A1 | | 11/1998 |
| WO | 2006049664 A1 | | 5/2006 |
| WO | 2007034451 A1 | | 3/2007 |

OTHER PUBLICATIONS

PCT Search Report and Written Opinion for PCT/CN2020/125265
dated Aug. 2, 2021, 12 pages.

* cited by examiner

300

330 330

300

330 330

100µm 10.0µm 200 um

FIG. 10C
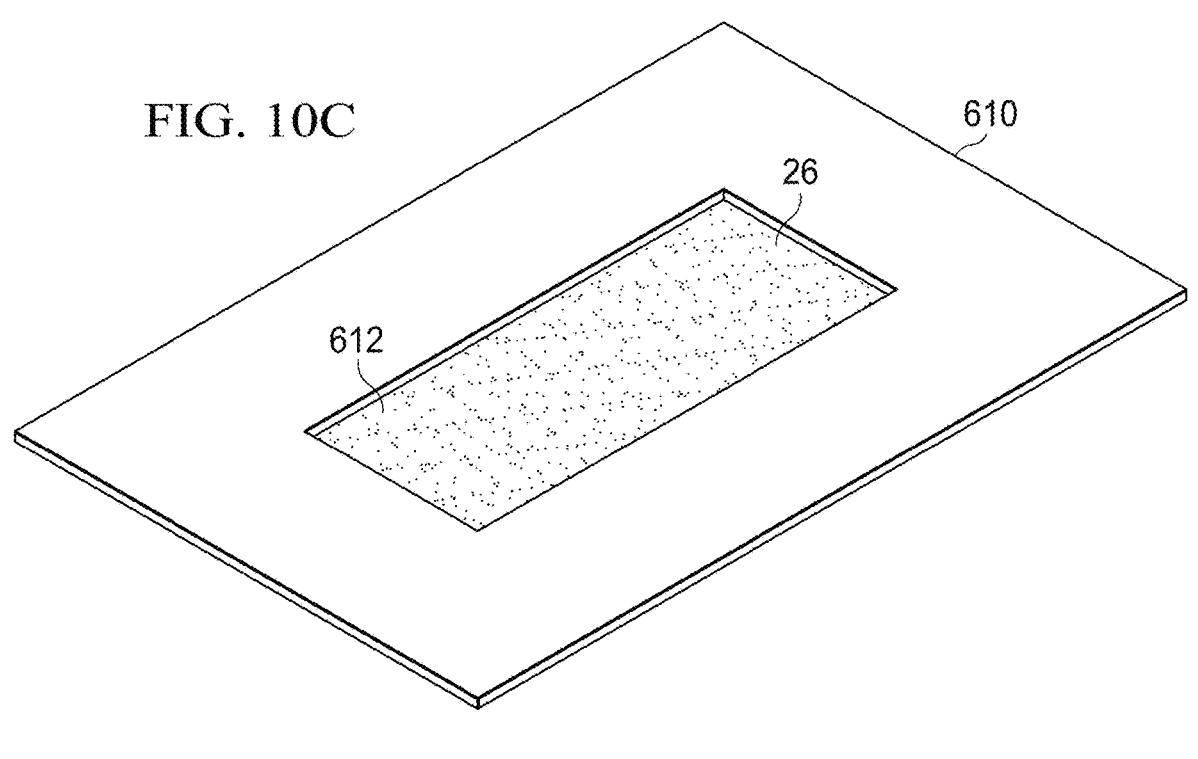
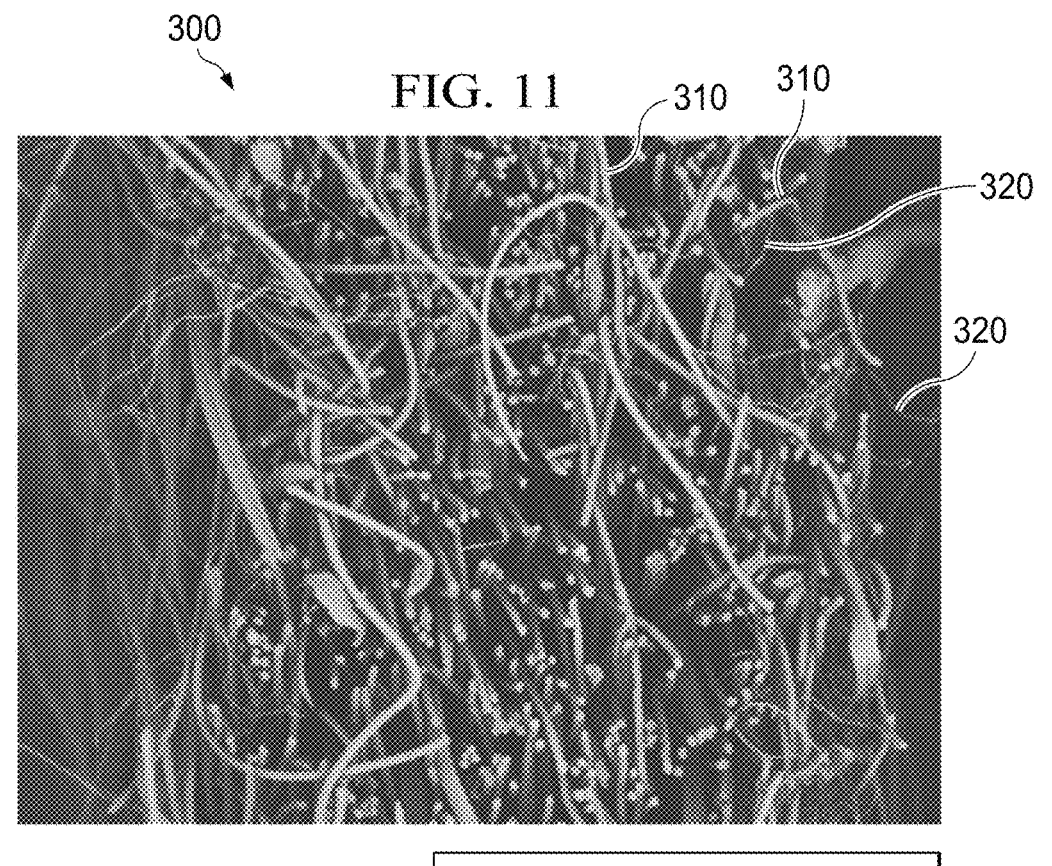
FIG. 11
200μm 200 um 200 um

300

310

310

320

320

200 um

300

310

310

320

320

1 mm

NONWOVEN AND ABSORBENT ARTICLES CONTAINING THE SAME

CROSS REFERENCE TO RELATED APPLICATION

This application claims priority under 35 U.S.C. § 119 to Chinese Patent Application No. PCT/2020/125265, filed on Oct. 30, 2020, the entire disclosure of which is hereby incorporated by reference.

FIELD

The present discloses generally relates to a nonwoven suitable for a disposable absorbent article, in particular a fluid management substrate that is a spunlace nonwoven comprising absorbent fibers and ultrafine fibers having improved performance characteristics, and an absorbent article comprising the same.

BACKGROUND

Disposable absorbent articles such as baby diapers, feminine hygiene products and incontinence products are designed to absorb fluids from the wearer's body. It is desirable in an absorbent article that the body fluid discharged on the topsheet rapidly transfer from a top surface of the topsheet towards the bottom of the topsheet which usually keep in close contact with an absorbent core of the absorbent article, so that the body fluid rapidly transfers from the topsheet into the absorbent core without giving a wearer uncomfortable feeling of wetness.

Disposable absorbent articles are generally designed to comprise a liquid pervious topsheet, a liquid impervious backsheet and an absorbent core disposed between the topsheet and the backsheet. So as not to prevent liquid transfer from a topsheet to an absorbent core and minimize an amount of body fluid remaining on the topsheet, absorbent articles have been designed by incorporating an acquisition-distribution system ("ADS") between a topsheet and an absorbent core. One desirable function of ADS is to quickly acquire liquids or other bodily exudates and transfer them to the absorbent core in an efficient manner Another one is to reduce the amount of liquid in a topsheet to avoid a wetness sensory. To reduce the liquid amount in a topsheet, an ADS material is required to have a good wicking property to distribute the liquid along a planar direction of the ADS material to lower the liquid concentration at the loading point and a high capillary force to suck the liquid from a topsheet. Both a wicking property and a capillary force are contributed by small pore sizes either in a planar direction or a z-direction. While small size pores in an ADS enhances wicking property and capillary force, it brings high flow resistance for the liquid to penetrate the ADS, which results in a slow acquisition speed.

Some currently marketed absorbent articles comprise an ADS comprising a nonwoven layer comprising synthetic fibers and/or water-absorptive fibers.

There is a continuous need for an ADS that moves fluid fast and away from body while it can reduce the liquid amount staying in a topsheet in absorbent articles.

SUMMARY

The present disclosure relates to an absorbent article comprising a liquid pervious topsheet, a liquid impervious backsheet, an absorbent core disposed between the topsheet and the backsheet, and an intermediate layer disposed between the topsheet and the absorbent core, the intermediate layer comprising a nonwoven, wherein the nonwoven comprises a plurality of apertures, absorbent fibers, and ultrafine fibers of about 3% to about 35% by weight of the nonwoven, and wherein at least most of the apertures have a hydraulic diameter in the range of about 600 μm to about 4500 μm.

The present disclosure also relates to an absorbent article comprising a liquid pervious topsheet, a liquid impervious backsheet, an absorbent core disposed between the topsheet and the backsheet, and an intermediate layer disposed between the topsheet and the absorbent core, the intermediate layer comprising a nonwoven, wherein the nonwoven comprises a plurality of apertures, absorbent fibers, and ultrafine fibers, wherein the absorbent fibers are staple fibers having a fiber length no less than about 30 mm, and wherein the nonwoven has an air permeability no less than about 110 $m^3/m^2/min$ as measured by Air Permeability Test, and a wicking rate no less than about 120 mm @ 300 s as measured by Wicking Rate Test.

The present disclosure also relates to a nonwoven comprising a plurality of apertures, absorbent fibers, and ultrafine fibers of about 3% to about 35% by weight of the nonwoven, and wherein the apertures have a hydraulic diameter in the range of about 600 μm to about 4500 μm.

The present disclosure also relates to a nonwoven comprising a plurality of apertures, absorbent fibers, and ultrafine fibers, wherein the nonwoven has an air permeability no less than 110 $m^3/m^2/min$ as measured by Air Permeability Test, and a wicking rate no less than about 120 mm @ 300 s as measured by Wicking Rate Test.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIGS. 10A-10C are schematic views of sample preparation and an exemplary apparatus used for a fluid acquisition time and a liquid amount in a topsheet.

FIG. 11 is an SEM image of cross-sectional view of a nonwoven (Sample 5) of present invention.

DETAILED DESCRIPTION OF THE INVENTION

Various non-limiting forms of the present disclosure will now be described to provide an overall understanding of the principles of the structure, function, manufacture, and use of an absorbent article comprising back ears having unique engineering strain properties and low surface roughness. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, feminine hygiene products such as sanitary napkins and pantyliners, and wipes.

As used herein, the term "absorbent fibers" intends to include fibers having a hydroscopic rate no less than about 8%.

As used herein, the term "cellulose-based fibers" intends to include both natural cellulose fibers such as pulp and cotton, and regenerated cellulose fibers such as rayon (including viscose, lyocell, MODAL (a product of Lenzing AG, Lenzing, Austria) and cuprammonium rayon unless specified differently.

As used herein, the terms "hydrophilic" and "hydrophobic" have meanings that are well established in the art with respect to the contact angle of water on the surface of a material. Thus, a material having a water contact angle of greater than about 90° is considered hydrophobic, and a material having a water contact angle of less than about 90° is considered hydrophilic.

As used herein, the term "natural fibers" refers to elongated substances produced by plants and animals and comprises animal-based fibers and plant-based fibers. Natural fibers may comprise fibers harvested without any postharvest treatment step as well as those having a post-treatment step, such as, for example, washing, scouring, and bleaching.

As used herein, the term "plant-based fibers" comprises both harvested fibers and synthetic fibers that comprise bio-based content. Harvested plant-based fibers may comprise cellulosic matter, such as wood pulp; seed hairs, such as cotton; stem (or bast) fibers, such as flax and hemp; leaf fibers, such as sisal; and husk fibers, such as coconut.

The term "Z-direction" means orthogonal to both the longitudinal and transverse directions.

Absorbent Article

Figure 1:
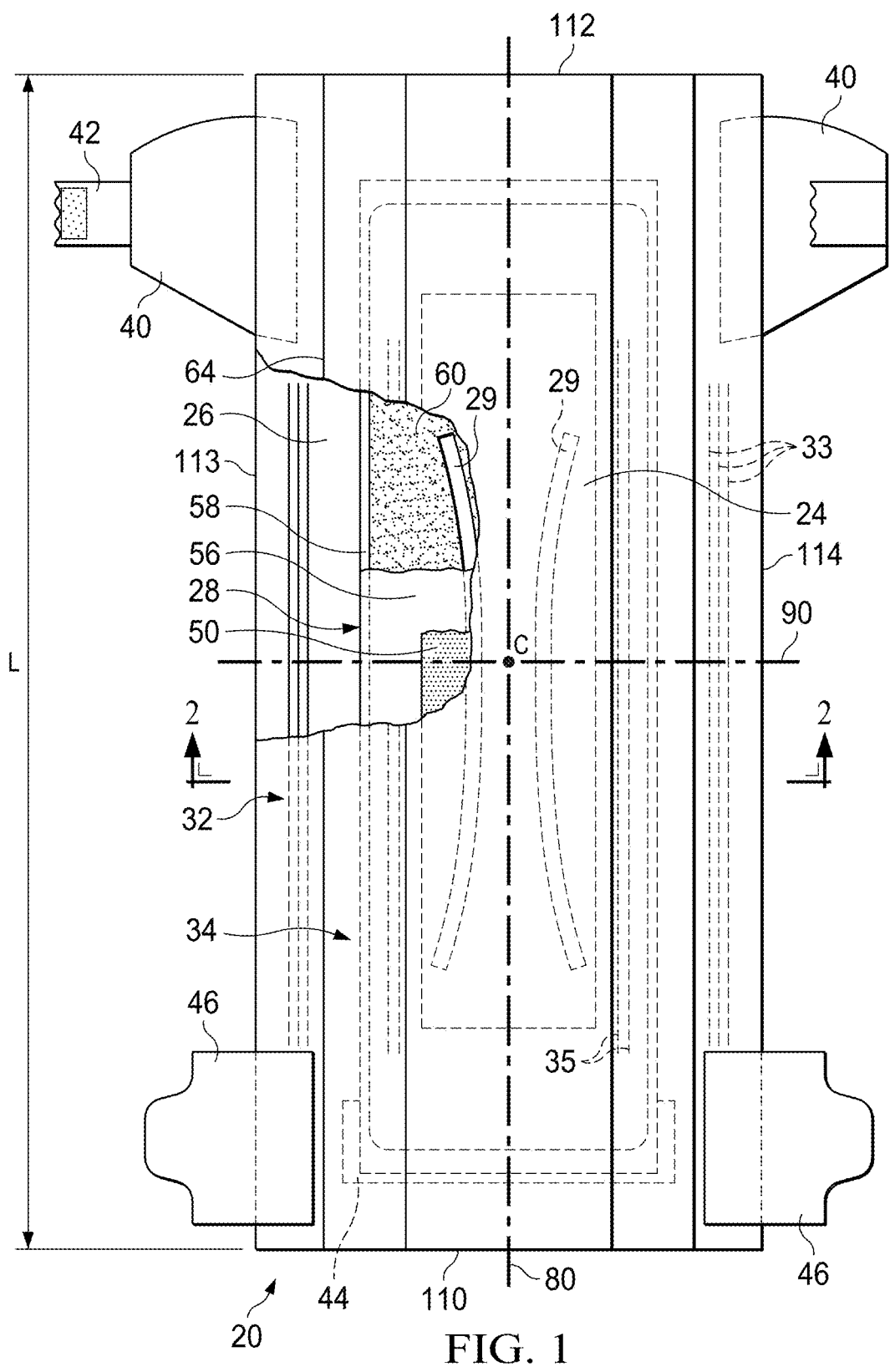
FIG. 1 is a schematic plan view of an exemplary absorbent article according to the present invention.

Absorbent articles will now be generally discussed and further illustrated in the form of a baby diaper 20 as exemplarily represented in FIG. 1. FIG. 1 is a plan view of the exemplary diaper 20 in a flattened-out configuration with the taped ends opened and the garment-facing side turned up. An article that is presented to the user closed such as a training pant may also be represented flattened out by cutting it along its side waists. The absorbent article will typically have a front edge 110, a back edge 112 and the longitudinally-extending lateral side edges 113, 114. The front edge 110 forms the edge of the front waist and the back edge 112 of the back waist, which together when worn by the wearer form the opening for the waist of the wearer. The lateral edges 113, 114 can each form one of the leg openings. The absorbent article 20 notionally comprises a longitudinal centerline 80 dividing the article in a left side and a right side, and a perpendicular transversal centerline 90 disposed at half the length of the article as measured on the longitudinal centerline 80, with both centerlines crossing at the center point C. The taped back ends 42 attached on the front of the diaper to such as a landing zone 44.

Figure 2:
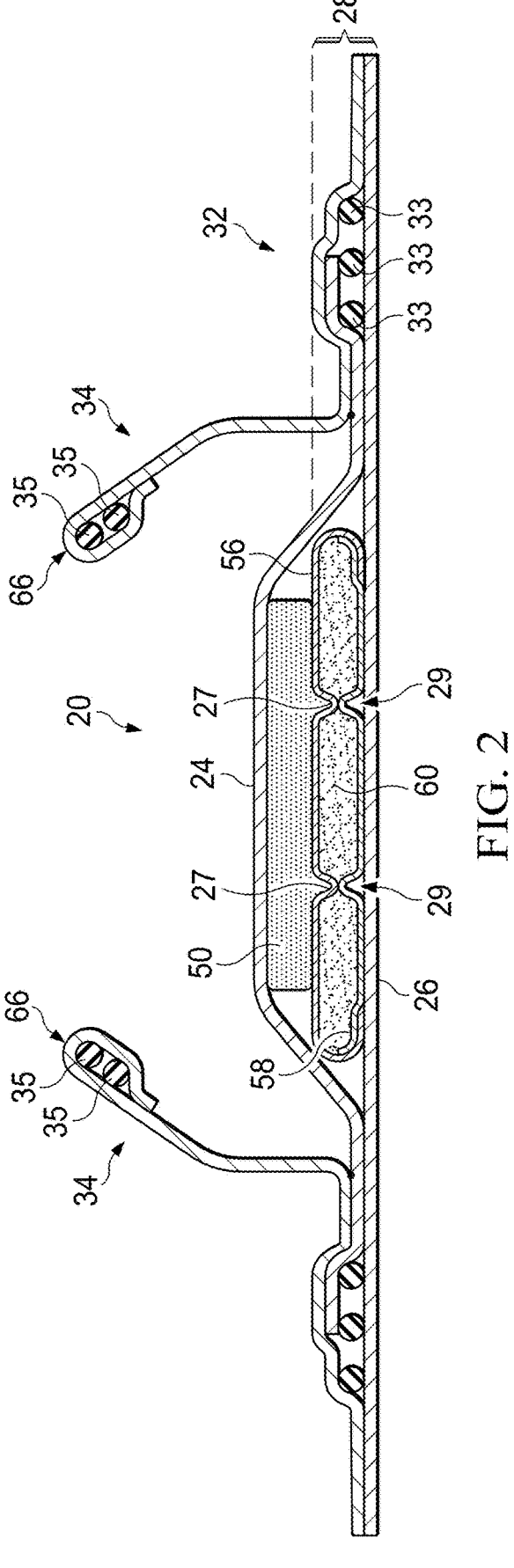
FIG. 2 is a lateral cross-section view along 2-2 of the absorbent article of FIG. 1.

Other layers of the absorbent article are better illustrated in FIG. 2, which shows in cross-section in addition to the liquid permeable topsheet 24 and the backsheet 26, an absorbent core 28 between the topsheet 24 and the backsheet 26.

An optional acquisition and/or distribution layer (or system) 50 is represented in FIG. 2 together with other typical diaper components. The acquisition and/or distribution layer may comprise one layer or more than one layer. Typical acquisition and/or distribution layers may not comprise SAP as this may slow the acquisition and distribution of the fluid, but an additional layer may also comprise SAP if some fluid retention properties are wished.

The absorbent article may typically comprise a pair of partially upstanding barrier leg cuffs 34 having elastic elements 35 and elasticized gasketing cuffs 32 having elastic elements 33 substantially planar with the chassis. Both types of cuffs are typically joined to the chassis of the absorbent article typically via bonding to the topsheet and/or backsheet.

The absorbent article may comprise elasticized back ears 40 having a tape end 42 which can be attached to a landing zone 44 at the front of the article, and front ears 46 typically present in such taped diapers.

Topsheet

Referring to FIGS. 1 and 2, a topsheet 24 is a part of the absorbent article 10 that is in contact with the wearer's skin. The topsheet 24 may be joined to portions of the backsheet 26, the absorbent core 28, the barrier leg cuffs 34, and/or any other layers as is known to those of ordinary skill in the art. The topsheet 24 may be compliant, soft-feeling, and non-irritating to the wearer's skin. Further, at least a portion of, or all of, the topsheet 24 may be liquid permeable, permitting liquid bodily exudates to readily penetrate through its thickness.

The topsheet may comprise one layer or more than one layer. The topsheet may comprise a plurality of three dimensional elements such as protrusion, recesses, apertures and any combination thereof, so that the topsheet has a three-dimensional structure.

A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers.

The topsheet may comprise a nonwoven comprising cellulose-based fibers. The topsheet may comprise a nonwoven layer comprising between about 20% and about 100%, between about 50% and about 100%, or between about 65% and 100%, by weight of cellulose-based fibers of the nonwoven layer. The topsheet may comprise about 100% cellulose-based fibers, such as about 100% cotton fibers. The topsheet may comprise a laminate comprising a nonwoven layer comprising cellulose-based fiber.

Absorbent Core

As used herein, the term "absorbent core" refers to a component used or intended to be used in an absorbent article and which comprises an absorbent material and optionally a core wrap. As used herein, the term "absorbent core" does not include the topsheet, the backsheet and any acquisition-distribution layer or multilayer system, which is not integral part of the absorbent core. The absorbent core is typically the component of an absorbent article that has the most absorbent capacity of all the components of the absorbent article. The terms "absorbent core" and "core" are herein used interchangeably.

Referring to FIGS. 1 and 2, the absorbent core 28 can absorb and contain liquid received by the absorbent article and comprise an absorbent material 60, which may be cellulose fibers, a blend of superabsorbent polymers and cellulose fibers, pure superabsorbent polymers, and/or a high internal phase emulsion foam. The absorbent core 28 may comprise absorbent material free channels 29, through which the top side 56 of the core wrap may be bonded to the bottom side 58 of the core wrap. The core wrap bonds 27 may at least persist as the absorbent core 28 swells upon liquid absorption and creates three-dimensional channels at the wearer-facing surface of the article. Of course, this is entirely optional, the absorbent core may also not have bonded channels, or even unbonded channels. The absorbent material defines an absorbent material area 8, which may be rectangular as show in in FIG. 1, but it is also common to have a shaped area which is tapered in the area around the transversal centerline 90.

The absorbent material comprises a liquid-absorbent material commonly used in disposable absorbent articles such as comminuted wood pulp, which is generally referred to as airfelt or fluff. Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (herein abbreviated as "SAP"), absorbent gelling materials, or any other known absorbent material or combinations of materials.

The absorbent material in the absorbent core can be any type. It can be an airfelt core comprising wood cellulose fibers such as pulp fibers mixed with SAP, or an airfelt-free core free from such cellulose fibers. Airfelt cores typically comprises from 40% to 80% of SAP. For absorbent cores comprising a relatively high proportion of SAP at least partially enclosed within the core wrap, the SAP content may represent in particular at least 80%, 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent core may comprise an absorbent material comprising at least 80%, at least 90%, at least 95%, or at least 99% by weight of the absorbent core. The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example.

Acquisition-Distribution System

Referring to FIGS. 1 and 2, the absorbent article 20 of the present disclosure comprises an acquisition-distribution system ("ADS") 50. One function of ADS 50 is to quickly acquire the body fluid such as urine and distribute them to the absorbent core 28 in an efficient manner. The ADS 50 comprises a nonwoven disclosed and be discussed in further detail below.

The ADS 50 may be a single layer. It may have two or more layers, which may form a unitary structure or may remain as discrete layers which may be attached to each other by, for example, thermal bonding, adhesive bonding or a combination thereof. A unitary structure herein intends to mean that although it may be formed by several sub-layers that have distinct properties and/or compositions from one another, they are somehow intermixed at the boundary region so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Typically, there is no adhesive used between the sub-layers of the unitary material. However, in some cases, adhesives and/or binders can be present although typically in a lower amount that in multilayer materials formed by separate layers.

In an absorbent article according to the present invention, the ADS comprises a nonwoven disclosed herein.

The ADS may have an air permeability no less than about 110 m³/m²/min to about 320 m³/m²/min as measured by Air Permeability Test and/or a wicking rate no less than about 120 mm @ 300 s as measured by Wicking Rate Test.

Further details regarding the nonwoven of disclosed herein used as a ADS discussed further in dedicated sections below.

Nonwoven

The nonwoven disclosed herein can be used in a variety of disposable absorbent articles, but is particularly useful in diapers, feminine hygiene products and incontinence products such as sanitary napkins and incontinence pads. The nonwoven of the present disclosure can be particularly effective as an acquisition-distribution system ("ADS") in absorbent articles.

Figure 3:
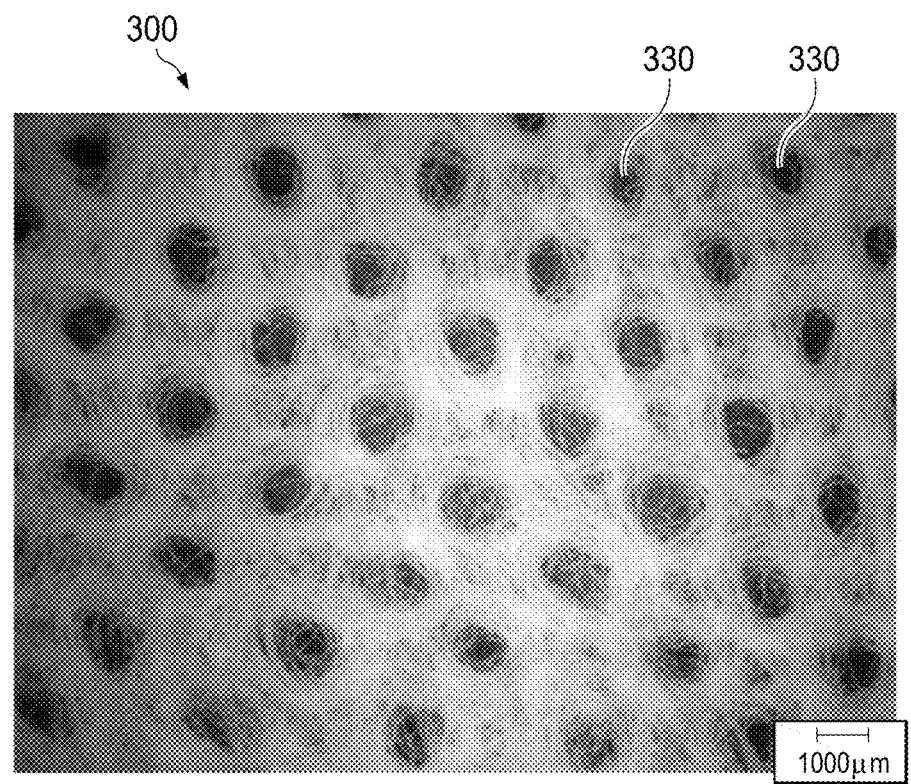
FIG. 3 is a microscopic image of a nonwoven of the present invention.
Figure 4:
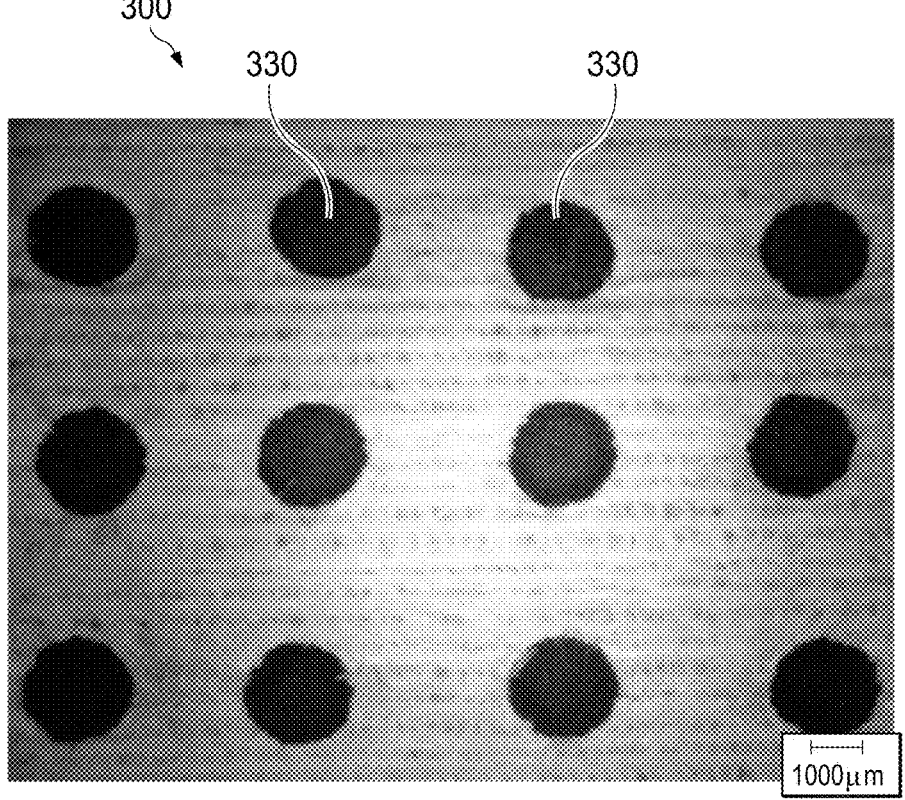
FIG. 4 is a microscopic image of another nonwoven of the present invention.

A nonwoven 300 disclosed herein, referring to FIGS. 3 and 4 comprises apertures 330. The nonwoven 300 disclosed herein, referring to FIGS. 5 and 6 which are SEM images of comprises absorbent fibers 310 and of ultrafine fibers 320.

The nonwoven of the present invention may comprise from about 65% to about 97% by weight, from about 70% to about 95% by weight or from about 80% to about 95% by weight, specifically including any values within these ranges and any ranges created thereby of absorbent fibers. Absorbent fibers are utilized to absorb liquid insults.

Any suitable absorbent fibers may be utilized. Some conventional absorbent fibers include cellulose-based fibers. Cellulose-based fibers suitable for the present invention may be staple fibers having a fiber length no less than about 30 mm, of about 30 mm to about 100 mm, or about 30 mm to about 50 mm or about 35 mm to about 50 mm, specifically reciting all values within these ranges and any ranges created thereby. The absorbent fibers may be regenerated cellulose fibers. In one embodiment, the absorbent fibers are viscose fibers.

As noted previously, in addition to absorbent fibers, the nonwoven of disclosed herein also comprises ultrafine fibers. The ultrafine fibers used in the present invention may be hydrophobic fibers. In the case where the ultrafine fiber is hydrophobic, the fiber itself absorbs little body fluid.

Ultrafine fiber may be formed using, for example, a meltblown spinning method or made by splitting splittable conjugate fibers. When the ultrafine fibers are formed by splitting splittable conjugate fibers, the splittable conjugate fibers make it possible to form the ultrafine fibers and entangle the ultrafine fibers and absorbent fibers tightly through hydroentanglement treatment, i.e. spunlace process, by high-pressure water streams. After the hydroentanglement treatment, the splittable conjugate fibers may not be completely split into the respective structural components. For example, splitting only a part of the structural components is acceptable. Alternatively, it is also acceptable that the ultrafine fiber is not a completely independent fiber and a single or a plurality of ultrafine fibers branch off of a single splittable conjugate fiber. In the case where the splitting of the splittable conjugate fiber into the ultrafine fibers is stopped halfway, the fibers split to ultrafine fibers incompletely are still considered ultrafine fibers.

Figure 7A:
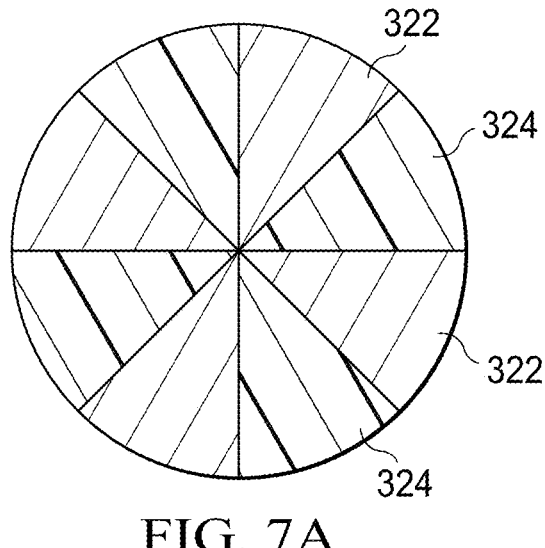
FIGS. 7A and 7B are diagrams illustrating exemplary cross-sectional configuration of splittable conjugate fibers
Figure 7B:
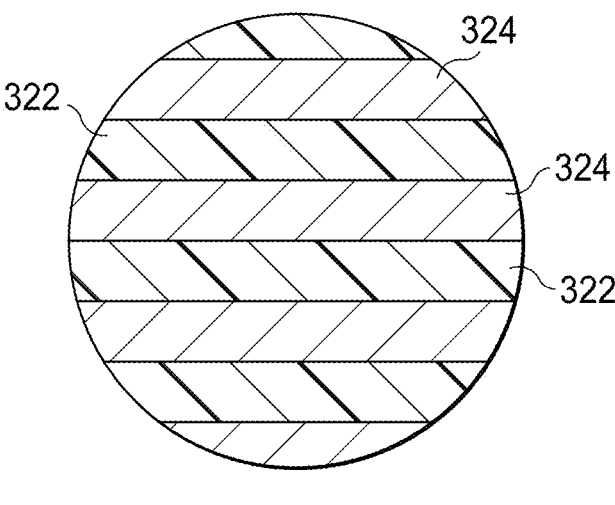

Referring to FIGS. 7A and 7B, the splittable conjugate fiber may have a fiber cross-section structure wherein at least one component is divided into two or more segments, and at least part of each component is exposed to the fiber surface, and the exposed portion is continuously formed in the longitudinal direction of the fiber. The splittable conjugate fibers each have a cross-sectional configuration as shown in FIG. 7A, for example, and include first plural segments 322 and second plural segments 324 which are circumferentially arranged in an alternating relation. The splittable conjugate fibers having such a configuration are split at interfaces of the polymeric segments 322 and 324 into split ultrafine fibers comprised of the polymeric segments 322 and 324 when impacts are applied to the conjugate fibers during a fiber splitting process such as hydroentanglement process.

The splittable conjugate fiber may comprise a combination of two polymers selected from polyethylene terephthalate ("PET"), polyester, polyethylene ("PE"), polypropylene ("PP"), ethylene propylene copolymer and polyamide ("PA"). The splittable conjugate fiber may comprise a combination of such as PET/PE, PET/PP, PET/PA, PET/ethylene propylene copolymer, PP/PE, or PA/PE.

The ultrafine fibers may have a diameter no greater than about 2 μm, or no greater than about 1.5 μm as measured by Fiber Diameter Test disclosed herein. If the fineness of the ultrafine fiber too high, it may not be effective to create a narrow space between absorbent fibers and ultrafine fiber to constrain liquid movement.

Without wishing to be bound by theory, the distance between absorbent fibers and ultrafine fibers may affect wicking rate of the nonwoven, and dry feel of an absorbent article comprising a nonwoven of the present invention. The ultrafine fibers do not have a strong water absorption property, and they may constrain body fluid to move away from the absorbent fibers when they exist closely near the absorbent fibers with a short distance to the absorbent fiber, and thus to enhance bonding strength between water absorbent fibers and water. Fiber diameter may affect a distance between absorbent fibers and ultrafine fibers.

For the formation of ultrafine fibers from splittable conjugate fibers, the number of the circumferentially arranged splittable segments in a splittable conjugate fiber may be about 8 to about 20 on the precondition that the splittable conjugate fiber having the cross-sectional configuration shown in FIGS. 7A and 7B may have a 1.5 denier to about 2.5 denier. If the number of the circumferentially arranged segments is increased, smaller diameter ultrafine fibers can be formed.

When the ultrafine fibers are staple fibers, a fiber length of the ultrafine fiber may be selected from a range of, for example, from about 5 mm to about 100 mm, or from about 20 mm to about 60 mm, or from about 30 mm to 60 mm.

The absorbent fibers and the ultrafine fibers of the nonwoven disclosed herein are densely entangled with each other, and the nonwoven has a high wicking rate. Accordingly, the nonwoven disclosed herein may be suitable for a component such as an acquisition and/or distribution layer in disposable absorbent articles.

When the liquid forms a continuous flow, driven by its gravity, the penetration speed follows Darcy's law, and a high permeability characterized by air permeability of an ADS is one factor to enable a high acquisition speed. At the downstream of the continuous flow, the liquid gravity cannot generate a sufficient pressure to drive the liquid to flow in a z-direction to the ADS, and a capillarity gradient plays a major role to drain the liquid down to the ADS from a topsheet. Therefore, a high capillary force of the ADS can result in a small amount of liquid retention in a topsheet and a dry sensory feel. The capillary force is characterized by a wicking rate.

As noted previously, in addition to absorbent fibers and ultrafine fibers, the nonwoven of the present invention also comprises a plurality of apertures having a hydraulic diameter in the range of about 600 μm to about 4500 μm. If the hydraulic diameter of apertures is too low, it negatively affects liquid penetration speed. If the hydraulic diameter of apertures is too high, connection between the nonwoven and other component such as a topsheet of an absorbent article when it is used as an ADS in an absorbent article, would decrease and result in a poor liquid drainage.

The nonwoven of the present invention may have a fiber mixing extent of no less than about 0.040, or less than 0.043, or less than 0.045 as measured by Fiber Mixing Extent Test disclosed herein. Without wishing to be bound by theory, the distance between absorbent fibers and ultrafine fibers may affect wicking rate of the nonwoven. The ultrafine fibers do not have a strong water absorption property, and they may constrain body fluid to move away from the absorbent fibers when they exist closely near the absorbent fibers with a short distance to the absorbent fiber, and thus to enhance bonding strength between water absorbent fibers and water.

The nonwoven may have a total open area from about 5% to about 21%. If a total open area % is too low, it negatively affects liquid penetration speed. If a total open area % is too high, connection between the nonwoven and other component such as a topsheet of an absorbent article when it is used as an ADS in an absorbent article, would decrease and result in a poor liquid drainage.

Nonwoven disclosed herein may have a basis weight no less than about 30 gsm, or no less than about 35 gsm, or no less than about 40 gsm. If nonwoven has a basis weight too low, a capillary gradient may not be generated effectively due to small amount of absorbent fibers.

The nonwoven disclosed herein may have an air permeability no less than 110 m³/m²/min, or no less than about 120 m³/m²/min, as measured by Air Permeability Test disclosed herein. If air permeability is too low, it negatively affects liquid penetration. Upper limit of air permeability may not be critical as higher air permeability is favorable in term of acquisition speed, and can be determined considering processability for an absorbent article production. For example, if the permeability of the nonwoven is too high, it is not effective to process in a vacuum conveying system in an absorbent article production. It may also cause a process failure as adhesive is easy to bleed through the nonwoven if permeability of the nonwoven is too high.

The nonwoven disclosed herein may have a wicking rate of no lower than 120 mm @ 300 s, as measured by Liquid in Topsheet Test disclosed herein. If wicking rate is too low, the nonwoven may not have a sufficient sucking power to draw down liquid from a topsheet and negatively affect dryness of a topsheet when the nonwoven is used as an ADS in an absorbent article.

Method for Producing Nonwoven

The nonwoven may be formed by any suitable process known in nonwoven industry. In one example, each of cellulose-based fibers and splittable conjugate fibers is fed into the fiber breaking unit, separately. The fiber breakers loosen the condensed fiber clusters into relatively loose fibers and laid down them on the same conveying belt according to a predetermined weight ratio. Then, these two fibers are conveyed into a fiber mixing container where the cellulose-based fibers and the splittable conjugate fibers are mixed. The fiber mixture is laid down by suitable processes for example, carding, airlaying, and wetlaying on a forming belt to form a web. The web may be processed to split the splittable conjugate fibers and entangle all constituent fibers by hydroentanglement with water jets (also known as spunlace) to obtain a nonwoven.

In another example, firstly splittable conjugate fibers are loaded into a water container. The hot alkali solution is used to treat the fibers for a certain time to split the splittable conjugate fibers into ultrafine fibers. After that, the alkali solution is drained away from this container, and the acid solution is added into the container to neutralize the free alkali. After that, the acid solution is drained away, and the pure water is added to rinse the fibers. Then, in the presence of water, viscose fibers are added into this container to mix with the ultrafine fibers according to the predetermined weight ratio. The fiber mixture is pulled out by a conveying belt into a web, and then goes through the spunlace unit for hydroentanglement to obtain a nonwoven. In this method, a fiber mixing speed, mixing time, and agitator design may be important to control the mixing extent between absorbent fibers and ultrafine fibers.

After the hydroentanglement, the nonwoven is optionally subjected to a drying step to further dry the nonwoven.

Apertures may be formed by spunlace process. Aperture size may be determined by a screen design and water jet pressure. Forming apertures in spunlace process is to balance aperture clarity and nonwoven strength. For having a desirable level of nonwoven strength, fibers need to be entangled firmly, but those firmly entangled fibers are difficult to be pushed by water on the big-mesh screen to form big apertures.

Figure 8:
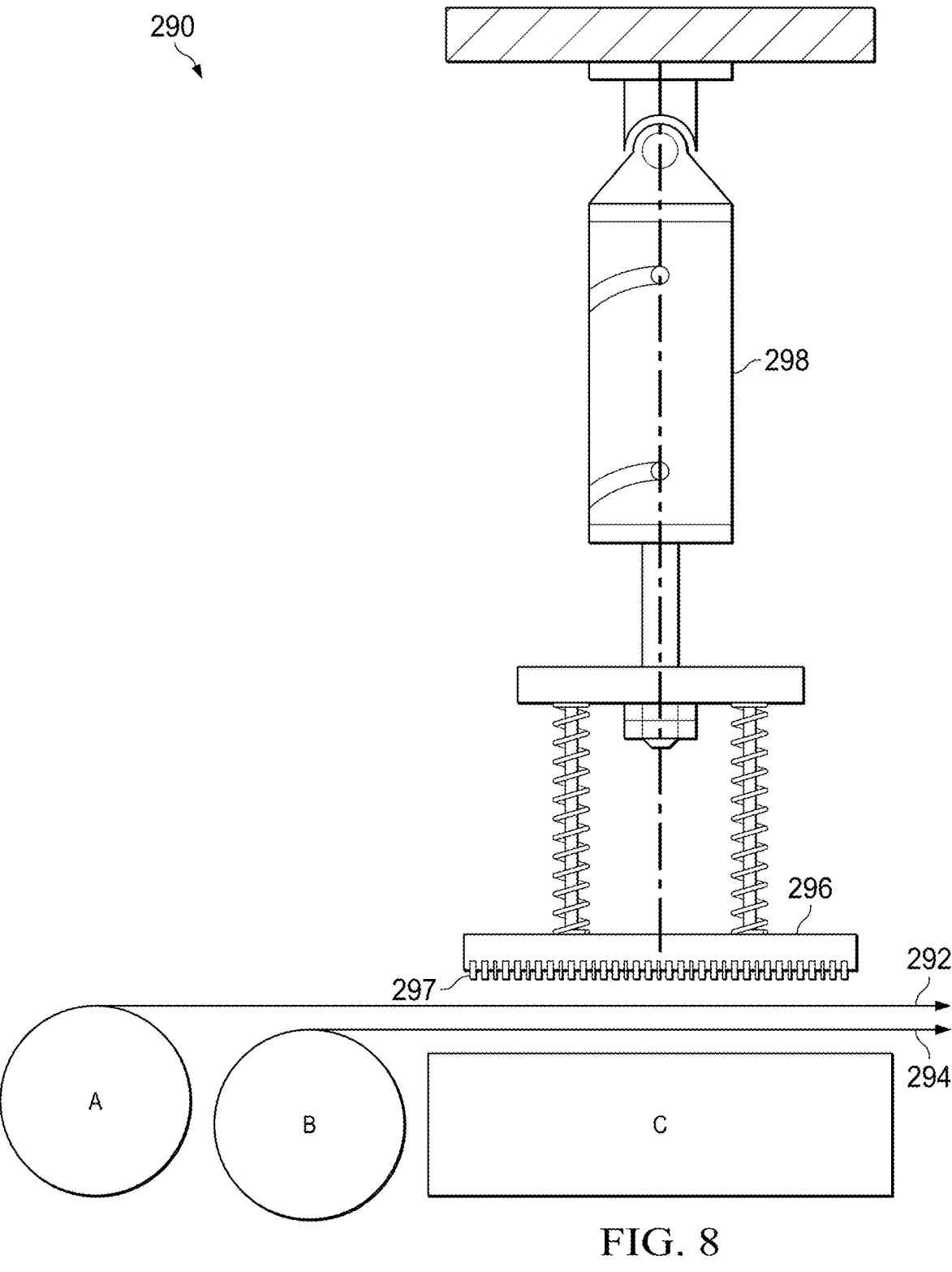
FIG. 8 is a schematic illustration of an apparatus for forming apertures in a nonwoven.

Apertures may be formed by post aperturing process known in the nonwoven industry after spunlace process. For example, apertures may be formed by a punch-aperturing process schematically illustrated in FIG. 8. First, a precursor nonwoven web 292 is fed, together with consumable material 294, into the punch unit 296 in a face-to-face manner. The precursor nonwoven web 292 may be unwound from roll A. The consumable material 294 may be unwound from roll B. The consumable material 294 may be of a greater stiffness than the precursor nonwoven web 292 and may be used to increase the stiffness of the precursor nonwoven web 292 during the aperturing process. The consumable material 294 may be, for example, paperboard with a stiffness greater than that of the precursor nonwoven web 292. This increase in stiffness may allow for creation of cleaner, more regular apertures with fewer, or no, aperture perimeter tails as compared to related art aperturing processes. In another example, the consumable material 294 may be replaced with an acquisition layer, wherein the precursor nonwoven web 292 and the acquisition layer may be unwound from their respective rolls and bonded together to form a laminate prior to entry into the punch unit 296. An actuator 298, such as a pneumatic actuator, for example, moves the punch unit 296, comprising a plurality of punch components 297, toward the precursor web to create apertures in the nonwoven web 292 and the consumable material 294. Punched pieces may then be at least partially removed, or fully removed, by directing a fluid, for example air, over the nonwoven web, or by placing the nonwoven web under vacuum (box C) after creation of the apertures in the nonwoven web. After the aperturing is complete, the nonwoven web may be wound or conveyed directly into a manufacturing operation for a consumer product, such as an absorbent article.

Measurement

1. SEM Image Test (1) Sample Preparation

When a nonwoven is available in a raw material form, a specimen with a size of 10 mm×20 mm is cut from the raw material. When a nonwoven is a component of a finished product, the nonwoven is removed from the finished product using a razor blade to excise the nonwoven from other components of the finished product and cut to provide a nonwoven specimen with a size of 10 mm×20 mm and free from folds or wrinkles. A cryogenic spray (such as Cyto-Freeze, Control Company, Houston Tex.) may be used to remove the nonwoven sample from other components of the finished product, if necessary.

For the measurement of a top view of a specimen, the specimen is adhered on a copper plate (40 mm diameter, 30 mm thickness) horizontally by double-sided conductive tape.

For the measurement of a cross section of a specimen, the specimen is firstly soaked in liquid nitrogen for 180 sec and then cut by a steel knife perpendicular to the specimen planar direction. After cutting, the specimen is adhered on a copper plate vertically by double-sided conductive tape, with the cut side facing up.

Then, the plate is placed in a sample chamber of a coating instrument (such as Hitachi E-1045) for platinum-spray coating. During coating, an air pressure in the sample camber is controlled to be lower than 100 Pa, and a charge currency is 300 mA. After coating for 120 sec, the copper plate is taken out.

(2) Image Generation

The coated specimen adhered on the copper plate is placed in the camber of SEM instrument (Hitachi TM3000) for measurement. For a top view image, an SEM image is obtained at a resolution sufficient to clearly elucidate absorbent fibers and ultrafine fibers present in the specimen. For a cross-section view image, an SEM image is obtained at a resolution sufficient to clearly elucidate the cross sections of the fibers present in the specimen.

2. Fiber Diameter Test

SEM images of cross section view of nonwoven samples are generated according to SEM Image Test above.

Fiber diameter is analyzed by the image analysis software, such as ImageJ software (version 1.52p or above, National Institutes of Health, USA) or equivalent. Open a measurement photo in ImageJ Convert the image type to 8-bit. The gray scale of the 8-bit image is 0 to 255. The fibers have high gray values, and the background has low gray levels.

Select an individual fiber part with a clean black background. Draw a line perpendicular to the fiber part and cross the fiber, whose length is about 2 times of the fiber width. Then, record the gray scale of each pixel on the line. The boundary between the fiber and background is defined as the pixel whose gray value is "$Gray_{min}+0.2\times(Gray_{max}-Gray_{min})$". The $Gray_{max}$ and $Gray_{min}$ are the maximum and minimal gray values on the line, respectively.

Then, the width of the fiber, considered as the fiber diameter, is identified to be the distance between two boundary points on the line. If the fiber is not perfect round, for example oval shape, the minimal dimension of the fiber such as the short axis is considered as the fiber diameter.

3. Hydroscopic Rate Test (1) Instrument

Balance: Accuracy of 0.001 g

Oven: Heating temperature control, accuracy 1° C.

Air fan: To circulate the air between internal and external for drying purpose;

(2) Procedure:

Take 50~55 g fibers and record the weight as G0.

Put loosely the fibers on a plate at 23° C. (+/−2° C.) and 50% RH (45~55% RH) for 24 hrs to reach equilibrium, and then record the weight as G1.

Turn on the oven and set the temperature as 108° C. When the temperature reaches 108° C. (+/−2° C.), put the fibers into the oven and stay for 40 mins.

After 40 min, take the fibers out of the oven to quickly weigh its weight within 60 s, and then put it back to the oven.

After every 10 mins, take the fibers out of the oven for weighing, and put them back to the oven again, until the difference between two consecutive measure results are less than 0.01 g. Record the final weight as G2.

The hydroscopic rate R is calculated as follows:

$$R=(G1-G2)/G2\times100\%.$$

4. Aperture Size Test (1) Sample Preparation

When a nonwoven is available in a raw material form, a specimen with a size of 50 mm×50 mm is cut from the raw material. When a nonwoven is a component of a finished product, the nonwoven is removed from the finished product using a razor blade and cut the nonwoven from other components of the finished product to provide a nonwoven specimen with a size of 10 mm×20 mm A cryogenic spray (such as Cyto-Freeze, Control Company, Houston Tex.) may be used to remove the nonwoven from other components of the finished product, if necessary.

(2) Image Generation

Microscopic images of the nonwoven are taken by using an optical microscope such as VR-3200 (KEYENCE, Japan) or equivalent. An appropriate magnification and working distance are chosen such that an individual aperture is suitably enlarged for measurement. The image should have enough resolution, at least 100 pixels across the aperture diameter.

(3) Image Analysis

The hydraulic diameter of the aperture is analyzed by the image analysis software, such as ImageJ software (version 1.52p or above, National Institutes of Health, USA) or equivalent. Open a measurement photo in ImageJ Convert the image type to 8-bit. The image needs to be distance calibrated with an image of the ruler to give an image resolution.

The 8-bit grayscale image is then converted to a binary image (with "black" foreground pixels corresponding to the aperture regions) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1}>P_t$ and $P_t\leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1}>P_t$ and $P_t\leq P_{t+1}$. This procedure identifies the gray level (GL) value for the minimum population located between the dark pixel peak of openings and the lighter pixel peak of the specimen material. If the histogram contains either zero or one local maximum, the method cannot proceed further, and no output parameters are defined.

Create a filtered image by removing small openings in the binary image using an outlier removing median filter, which replaces a pixel with median of the surrounding area of 5 pixels in radius if the pixel is darker than the surrounding. Create a second filtered image based on the first one by removing stray fibers in the binary image using an outlier removing median filter, which replaces a pixel with the median of the surrounding area of 5 pixels in radius if the pixel is brighter than the surrounding. Set the measurements to include the analysis of aperture area (A) and perimeter (L). Obtain the area and perimeter of the selected openings ("quality apertures") after tracing openings by their outer edge and excluding the openings with the size below 2000 µm².

The hydraulic diameter is calculated by 4×A/L.

5. Open Area Test

Aperture open area percentage measurement is performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, VA) is used as the background for the scanned images.

Take the steel frame and place double-sided adhesive tape on the bottom surface surrounding the interior opening. To obtain a specimen, lay the nonwoven flat on a lab bench. Using a double-sided conductive tape, adhere the steel frame to the nonwoven. Measurements can also be made on test samples obtained from a nonwoven removed from an absorbent article. A cryogenic spray (such as Cyto-Freeze, Control Company, Houston Tex.) or other suitable solvents that do not permanently alter the properties of the nonwoven specimen composition may be used to remove the nonwoven from other components of the absorbent article if necessary.

When excising the material layer from an absorbent article, use care to not impart any contamination or distortion to the layer during the process. If the material layer has been excised from an absorbent article, a test location is the intersection of the midpoints of the longitudinal axis and lateral axis of the absorbent article.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed. Place the black glass tile on top of the frame covering the specimen, close the lid and acquire a scanned image. In like fashion scan the remaining four replicates.

Open the calibration file in ImageJ and perform a linear calibration using the imaged ruler, with the scale set to Global so that the calibration will be applied to subsequent specimens. Open a specimen image in ImageJ View the histogram and identify the gray level value for the minimum population located between the dark pixel peak of the holes and the lighter pixel peak of the nonwoven. Threshold the image at the minimum gray level value to generate a binary image. In the processed image, the apertures appear as black and nonwoven as white.

Select the analyze particles function. Set the minimum aperture area exclusion limit to 0.02 mm2 and for the analysis to exclude the edge apertures. Set the software to calculate effective aperture area. Record the average effective aperture area to the nearest 0.01 mm². Again, select the analyze particles function, but this time set the analysis to include the edge holes as it calculates the effective aperture areas. Sum the effective aperture areas (includes whole and partial apertures) and divide by the total area included in the image (2500 mm2) Record as the open area percentage to the nearest 0.1%.

6. Fiber Mixing Extent Test

Fiber mixing extent is determined using scanning electron microscopy (SEM) image analysis of cross section of a nonwoven. The analysis procedure is described below.

Input image: SEM images of cross section view of nonwoven samples are generated according to SEM Image Test above.

Figure 9A:
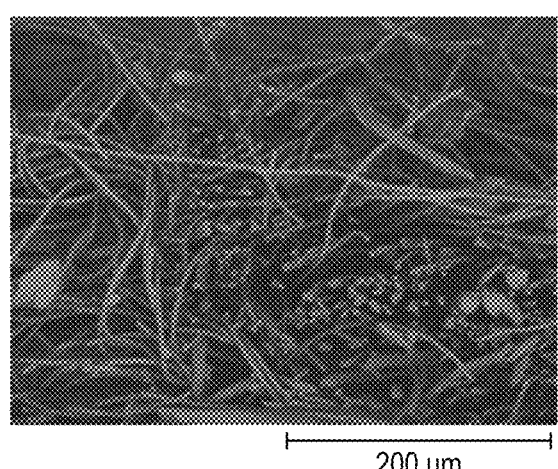
FIG. 9A is an SEM image of a cross-sectional view of a nonwoven to calculate a fiber mixing extent according to Fiber mixing extent Test.

Image recognition: FIG. 9A is an SEM image (magnification of 500×) of a cross-sectional view of a nonwoven.

Figure 9B:
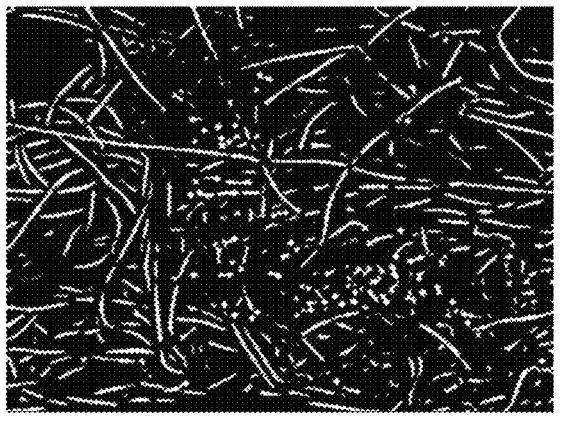
FIG. 9B is a binary image of manually labeled absorbent fibers generated based on FIG. 9A.
Figure 9C:
FIG. 9C is a binary image of manually labeled ultrafine fibers generated based on FIG. 9A.

Referring to FIGS. 9A-9C, absorbent fibers and ultrafine fibers are manually recognized in FIG. 9A and separately labeled to two binary images. FIGS. 9B and 9C are a binary image of absorbent fibers, and a binary image of ultrafine fibers, with the same size of view field, respectively.

Fiber density calculation for grids and absorbent fibers/ultrafine fiber ratio matrix:

a. Total density $$(\eta_{thick}^{tot})$$

of absorbent fibers is calculated by dividing the total absorbent fiber pixel number by number of total pixels of the image.

b. Both thick and fine fiber images are divided to 32 micrometer width square grids. For each grid, fiber density of both thick and fine are calculated $$(\eta_{thick}^{i} \text{ and } \eta_{fine}^{i})$$

by dividing the fiber pixel number by number of total pixels of each grid.

c. the fine to absorbent fiber ratio of each grid ($R_i$) is calculated by $$\frac{\eta_{fine}^{i}}{\eta_{thick}^{i}}.$$

However, if $$\eta_{thick}^{i}$$

is smaller than half of the total absorbent fiber density $$\eta_{thick}^{tot},$$

this ratio will be set to zero.

d. the fiber mixing extent ratio "R" is calculated by averaging all the $R_i$ for this image.

For each nonwoven sample, 10 SEM images of different nonwoven cross section parts are tested. The reported value is the average of the 10 recorded measurements for each nonwoven sample.

7. Air Permeability Test

Air permeability of nonwoven is measured using European Disposables and Nonwovens Association (EDANA) 140.2-99 with modifications below.

(1) Analysis area: 38.3 cm²,
(2) Pressure drop: 125 Pa, and
(3) Report unit: m³/m²/min 8. Wicking Rate Test The measurements for wicking rate provided herein were obtained by using European Disposables and Nonwovens Association (EDANA) Test Method 70.1.

9. Fluid Acquisition Test

Figure 10A:
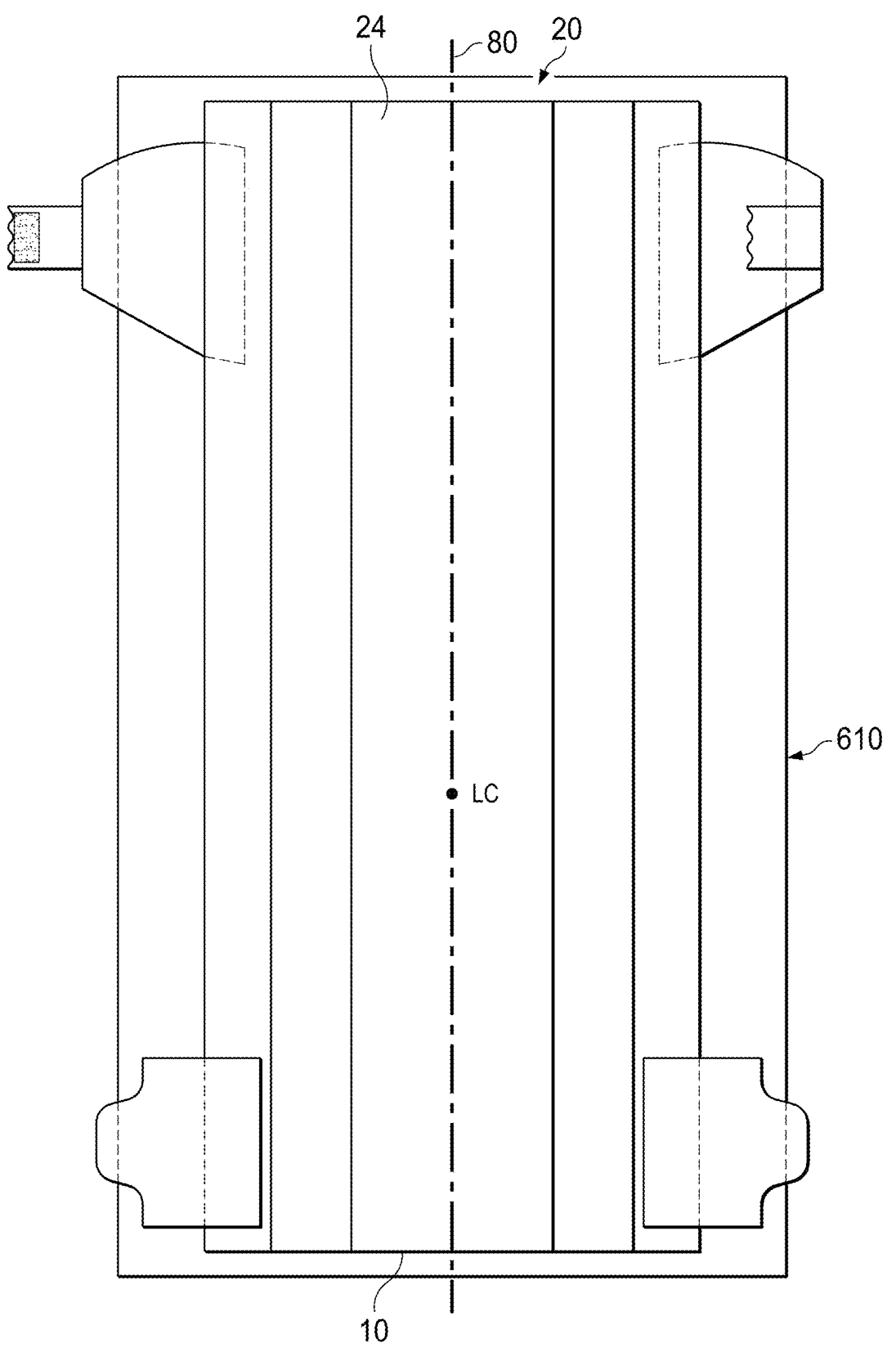
Figure 10B:
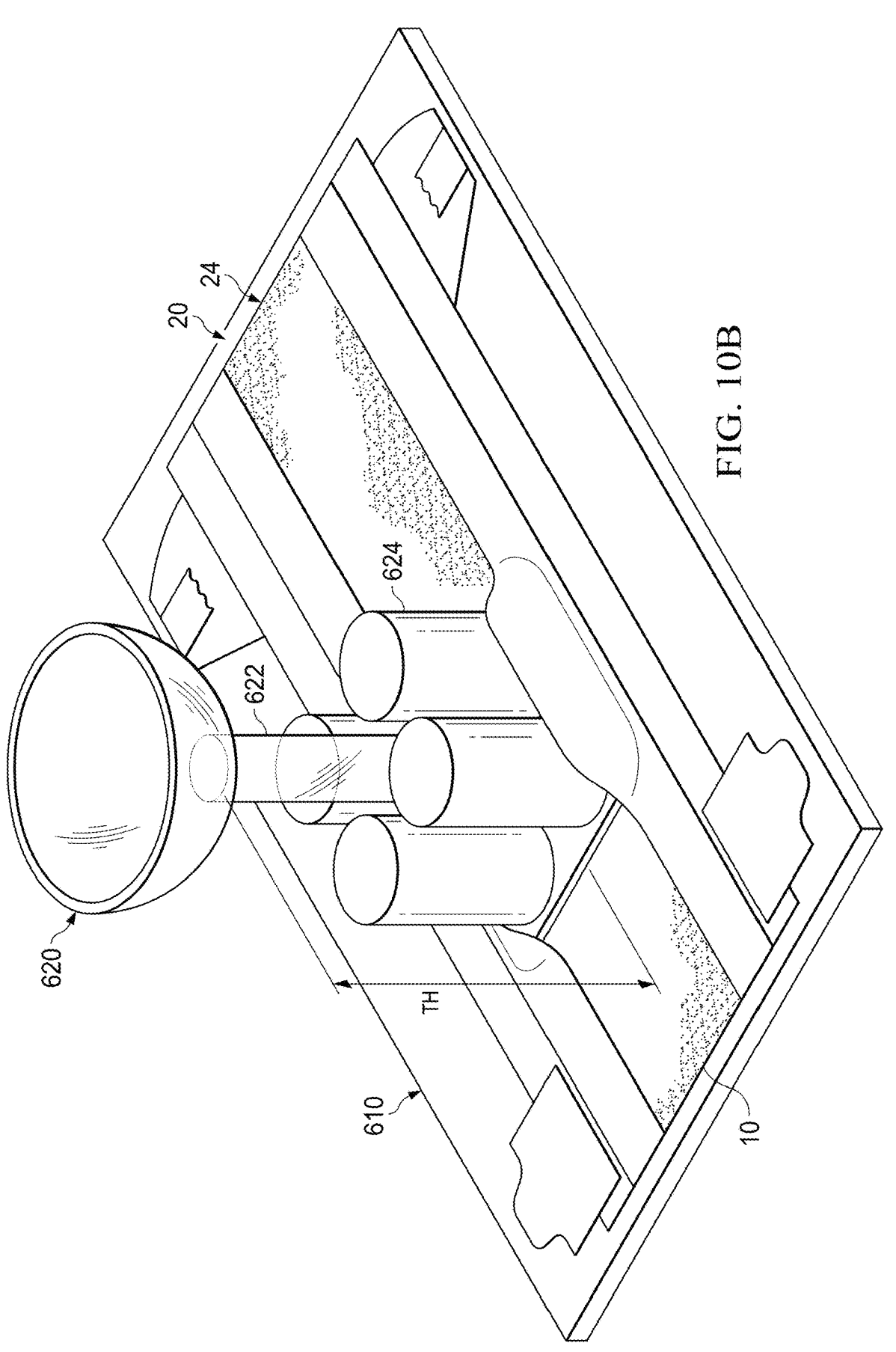

Referring to FIGS. 10A-10C, lay a sample absorbent article 20 on a bench plate 610 having a 250 mm by 400 mm having a hollow part 612 in the middle of the plate with a topsheet 24 facing upward. Attach a front edge side and a back edge side of the absorbent article 20 to the plate 610 using a hook material, adhesive tape or the like. Draw a longitudinal centerline 80. The loading center LC of a loading location is along the longitudinal centerline 80, and distanced 12 cm away from a front edge 10 of the absorbent article 20.

Place a loading tool 620 on top of loading location in such a way that the loading center LC is located in the middle of the loading tube 622. The weights 624 (500 g per each) on the loading tool 620 creates ~0.3 psi pressure. The equilibration time before dosing the first loading is 5 minutes. Load a first gush of 75 ml of 0.9% saline solution through the loading tube 622. The equilibration time between consecutive loadings is 5 minutes. Load a second gush of 75 ml of 0.9% saline solution, and a third gush of 75 ml of 0.9% saline solution are loaded in the same manner as the first gush. During each gush, when the liquid is loaded into the loading tool, the timer starts. When the liquid height in the tube 622 is lower than 0.5 mm, the timer stops. This time is recorded as the acquisition time of one gush, i.e. Ti (i=1, 2, or 3). Total acquisition time is obtained according to equation (1) below.

$$\text{Total acquisition time } T_{total}=T1+T2+T3 \qquad (1)$$

10. Liquid in Topsheet Test

Liquid amount in a topsheet is measured using samples in the Fluid Acquisition Time Test above. Before the first gush, a topsheet is removed from underling layers of the sample absorbent article carefully. A cryogenic spray (such as Cyto-Freeze, Control Company, Houston Tex.) or other suitable solvents may be used to remove the topsheet from the underling layers if necessary. A dry weight of the topsheet is weighed and recorded as W0. Then, the removed topsheet is reattached to the underling layers of the sample absorbent article using 1 gsm glue. After the $3^{rd}$ gush according to the Fluid Acquisition Time Test, the loading tool is kept on the topsheet for 5 min before removing. Then, the topsheet is carefully removed from the sample absorbent article for weighing. Weight of the topsheet is recorded as W1. Liquid in topsheet is calculated according to equation (2) below.

$$\text{Liquid in topsheet}=W1-W0 \qquad (2)$$

EXAMPLES

Example 1: Nonwovens

Nonwoven samples were produced and analyzed regarding a variety of characteristics according to methods described in the MEASUREMENT section above. Results are summarized in Table 1.

Sample 1: A 58 gsm apertured spunlace material was produced from 95% by weight 1.7 dtex viscose fibers (fiber length: 40 mm, hydroscopic rate: about 11%) and 5% by weight 2 denier splittable PET/PA composite fibers (fiber length: 38 mm, 8 segments for each of PET and PA, PET/PA=60/40 by weight %) using carding-spunlace process with a 100 mesh screen. Apertures had a hydraulic diameter of 180 μm.

Figure 5:
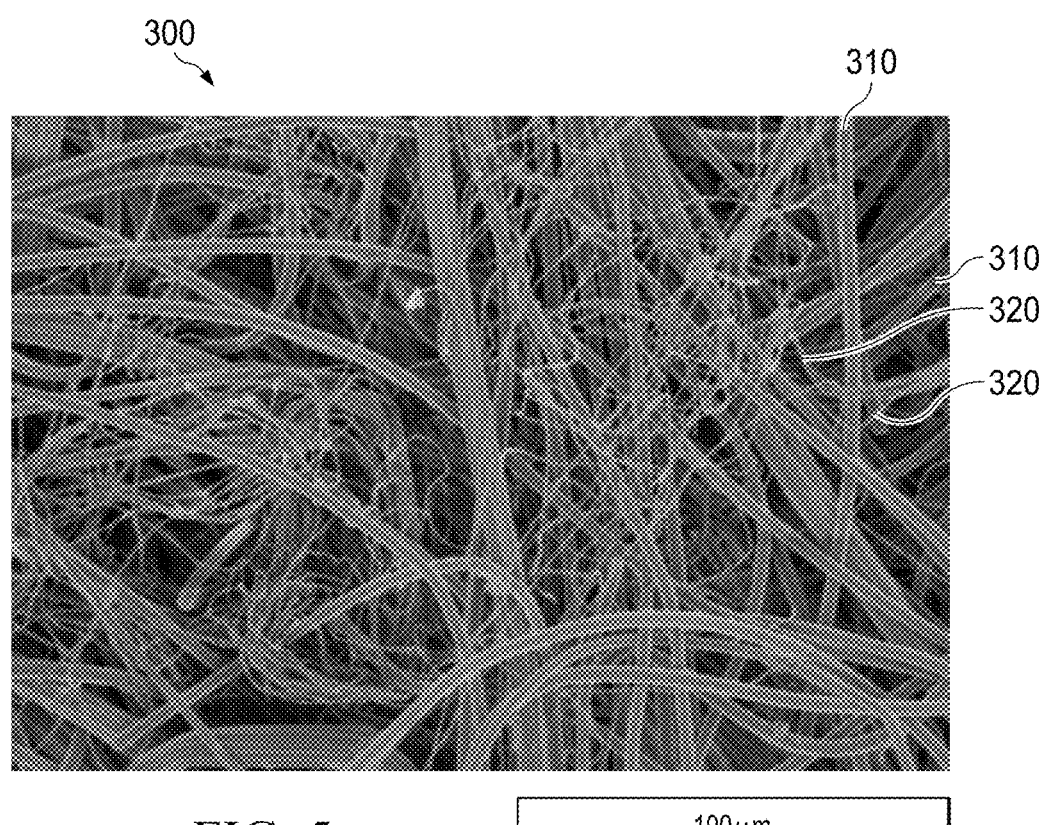
FIG. 5 is an SEM image of plan view of a nonwoven (Sample 6) of the present invention.
Figure 6:
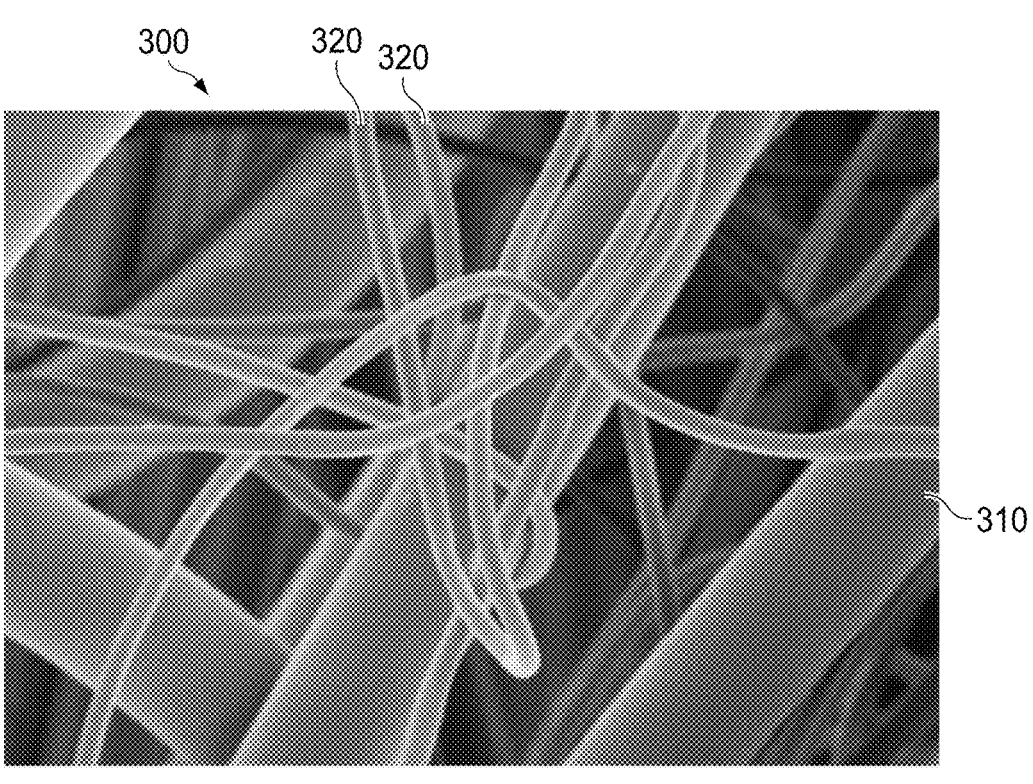
FIG. 6 is a magnified SEM image of plan view of the same nonwoven as FIG. 5.
Figure 12:
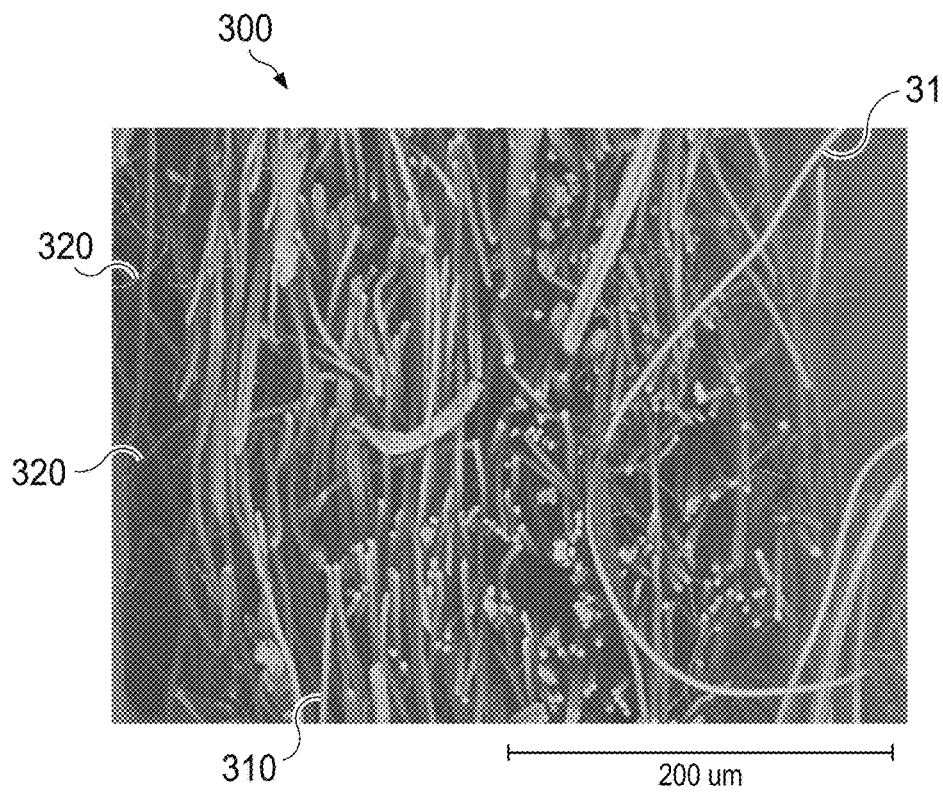
FIG. 12 is an SEM image of cross-sectional view of a nonwoven (Sample 6) of the present invention.
Figure 13:
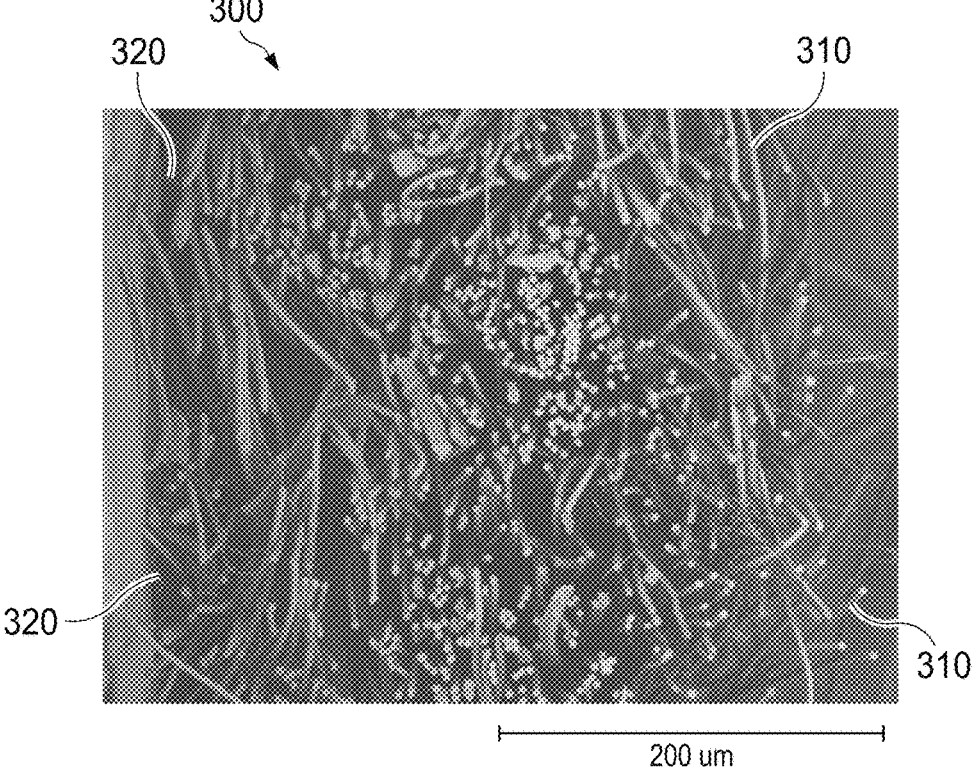
FIG. 13 is an SEM image of cross-sectional view of a nonwoven (Sample 10) of the present invention.

Samples 2-14: Apertured spunlace materials from the same viscose fibers and splittable PET/PA fibers as used for Sample 1 in various ratios and having various aperture sizes as indicated in Table 1 were produced using carding-spunlace process and post aperturing process. In Samples 2-8, apertures were formed by spunlace process with appropriate mesh screens. In Samples 9-11, 13 and 14, apertures were formed using punching aperturing process disclosed herein. FIGS. 5 and 6 are SEM images of plane views of Sample 6. FIGS. 11-13 are SEM images (Image resolution: about 0.04 μm/pixel) of cross section views of Samples 5, 6 and 10, respectively.

Figure 14:
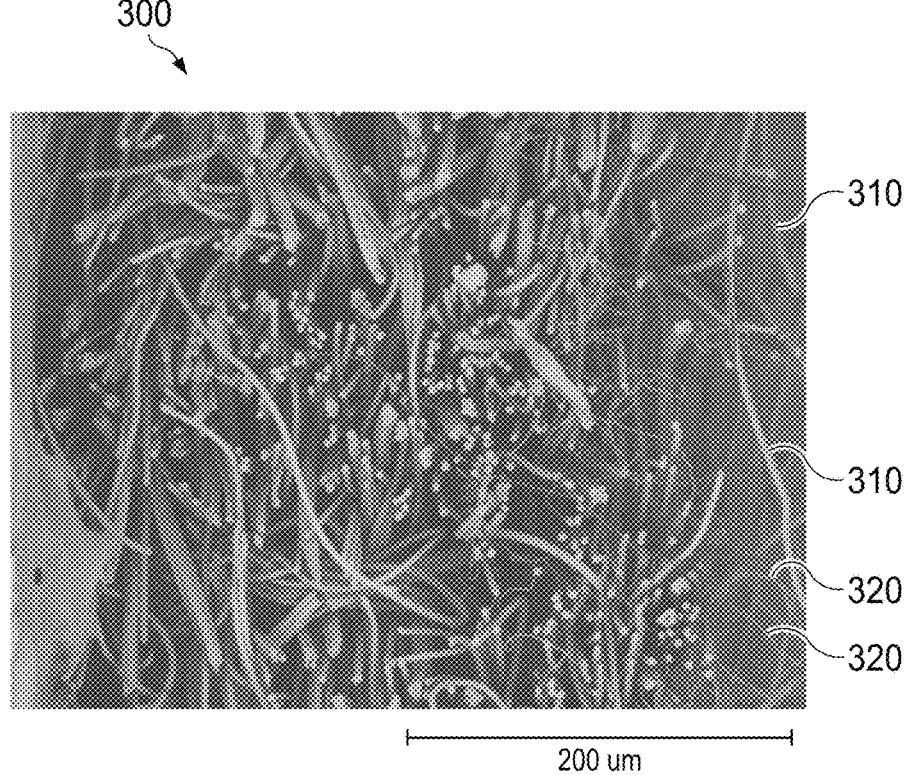
FIG. 14 is an SEM image of cross-sectional view of a nonwoven (Sample 15).

Sample 15: A 60 gsm apertured spunlace material comprising 90% by weight viscose fibers (fiber length: fiber fineness:), and 10% by weight ultrafine PET fibers and PA fibers was produced using carding-spunlace process to have apertures with a hydraulic diameter of 670 μm. FIG. 14 is an SEM image of a cross section view of Sample 15.

Sample 16: A 60 gsm apertured spunlace material with an aperture size of 180 μm was produced from 90% by weight cotton fibers (fiber length: 22-28 mm, hydroscopic rate: about 6%) and 10% by weight the same splittable PET/PA composite fibers as used for Sample 1 using carding-spunlace process with a 100 mesh screen.

Sample 17: A 60 gsm apertured spunlace material with an aperture size of 920 μm was produced from the same cotton fibers and splittable PET/PA composite fibers (90:10 by weight %) as used for Sample 16, using carding-spunlace process. Apertures having a hydraulic diameter of 920 μm were formed using punching aperturing process disclosed herein.

Sample 18: A 55 gsm apertured spunlace material comprising 100% 1.7 dtex viscose fibers (fiber length: 40 mm, hydroscopic rate: 10%-12%) with a hydraulic diameter of 180 μm was produced using carding-spunlace process with a 100 mesh screen.

Samples 19-22: Apertured spunlace materials from 1.7 dtex viscose fibers (fiber length: 40 mm, hydroscopic rate: 10%-12%) and PET fibers in various ratios and having various aperture sizes as indicated in Table 1 were produced using carding-spunlace process with a 100 mesh screen. Apertures had a hydraulic diameter of 180 μm.

Sample 23: 40 gsm air-through carded nonwoven (Z87G from Xiamen Yanjan New Material Co. Ltd, China) from 2 denier PE/PET bicomponent fibers and 4 denier PE/PET bicomponent fibers (60:40 by weight %).

Sample 24: 43 gsm nonwoven (AQL2+ from TWE Nonwoven (Hangzhou) Co. Ltd, China)

Sample 25: 80 gsm laminate nonwoven (B643H080N00B from Fitesa, China) having a 20 gsm hydrophilic air through nonwoven top layer and a 60 gsm air-laid pulp bottom layer.

Figure 15:
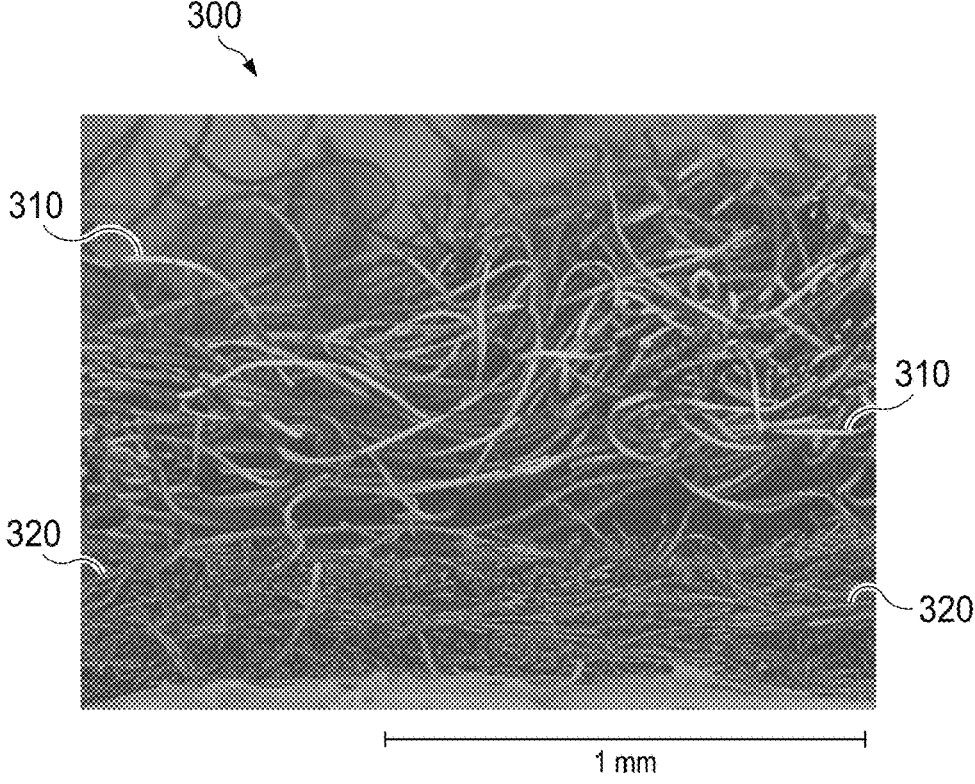
FIG. 15 is an SEM image of cross-sectional view of a nonwoven (Sample 26).

Sample 26: A nonwoven laminate having a top layer of 60 gsm viscose layer and a bottom layer of 20 gms ultrafine fiber layer was produced. The viscose layer was made from the same viscose fibers as used for Sample 1 using carding-spunlace process with a 100 mesh. The ultrafine fiber layer was made from the same splittable conjugate fibers as used for Sample 1 using carding-spunlace process. The viscose layer and the ultrafine fiber layer were laminated using 2 gsm adhesive. Then, apertures with a hydraulic diameter of 670 μm were formed in the laminate using punching aperturing process. FIG. 15 is an SEM image (Image resolution: about 0.04 μm/pixel) of cross section view of Sample 26.

Sample 27: A nonwoven laminate having a top layer of 20 gsm ultrafine fiber layer and a bottom layer of 60 gsm viscose fiber layer was produced. The ultrafine fiber layer was made from the same splittable conjugate fibers as used for Sample 1 using carding-spunlace process. The viscose layer made from the same viscose fibers as used for Sample 1 using carding-spunlace process with a 100-mesh screen. The viscose layer and the ultrafine fiber layer were laminated using 2 gsm adhesive. Then, apertures with a hydraulic diameter of 670 μm were formed in the laminate using punching aperturing process.

Example 2: Nonwoven Characteristics

Aperture diameters, open areas, air permeabilities and wicking rates of nonwovens prepared in Example 1 were measured according to Aperture Size Test, Open Area Test, Permeability Test and Wicking Rate Test disclosed herein, respectively, and are indicated in Table 1. Fiber mixing extent of nonwovens 6, 10, 15 and 26 prepared in Example 1 was measured according to Fiber Mixing Extent Test disclosed herein, and is indicated in Table 1.

TABLE 1

| Nonwoven Substrate Sample | Basis weight (gsm) | Constituent fibers | Aperture diameter* (μm) | Open area (%) | Air permeability ($m^3/m^2/min$) | Wicking rate (mm at 300 sec) | Fiber Mixing Extent |
|---|---|---|---|---|---|---|---|
| 1 | 58 | 95% viscose, 5% ultrafine fiber* | 180 | 1.5% | 56 | 183 | |
| 2 | 55 | 90% viscose, 10% ultrafine fiber | 180 | 1.2% | 50.6 | 185 | |
| 3 | 59 | 80% viscose, 20% ultrafine fiber | 180 | 1.3% | 63.6 | 167 | |
| 4 | 60 | 70% viscose, 30% ultrafine fiber | 180 | 1.5% | 71 | 143 | |
| 5 | 60 | 95% viscose, 5% ultrafine fiber | 670 | 6.9% | 116.5 | 189 | |
| 6 | 60 | 90% viscose, 10% ultrafine fiber | 670 | 7.3% | 121.5 | 187 | 0.062 |
| 7 | 60 | 80% viscose, 20% ultrafine fiber | 670 | 6.5% | 128 | 165 | |
| 8 | 60 | 70% viscose, 30% ultrafine fiber | 670 | 6.7% | 121 | 122 | |
| 9 | 60 | 95% viscose, 5% ultrafine fiber | 920 | 11.6% | 210 | 178 | 0.060 |
| 10 | 60 | 95% viscose, 5% ultrafine fiber | 1840 | 14.4% | 245 | 177 | 0.052 |
| 11 | 60 | 95% viscose, 5% ultrafine fiber | 4180 | 19.9% | 300 | 175 | |
| 12 | 60 | 60% viscose, 40% ultrafine fiber | 670 | 6.9% | 154 | 117 | |
| 13 | 60 | 95% viscose, 5% ultrafine fiber | 5220 | 22.6% | 343 | 143 | |
| 14 | 58 | 95% viscose, 5% ultrafine fiber | 590 | 6.0% | 105 | 185 | |
| 15 | 60 | 90% viscose, 10% ultrafine fiber | 670 | 6.9% | 107 | 142 | 0.033 |
| 16 | 60 | 90% cotton, 10% ultrafine fiber | 180 | 1.5% | 60 | 147 | |
| 17 | 60 | 90% cotton, 10% ultrafine fiber | 920 | 12.5% | 199 | 140 | |
| 18 | 55 | 100% viscose | 180 | 1.2% | 69.9 | 145 | |
| 19 | 54 | 90% viscose, 10% PET/PA bico fiber | 180 | 1.3% | 73.1 | 144 | |
| 20 | 60 | 80% viscose, 20% PET/PA bico fiber | 180 | 1.2% | 71.2 | 143 | |
| 21 | 55 | 70% viscose, 30% PET/PA bico fiber | 180 | 1.4% | 77.2 | 147 | |
| 22 | 55 | 60% viscose, 40% PET/PA bico fiber | 180 | 1.3% | 109.5 | 103 | |
| 23 | 40 | 100% PE/PET bico fiber | NA | NA | 249.5 | 40 | |
| 24 | 43 | | NA | NA | 234 | 48 | |
| 25 | 80 | | NA | NA | 88 | 75 | |
| 26 | 80 | Top: 60 gsm viscose Bottom: 20 gsm PET and PA ultrafine fibers | 670 | 7.0% | 99.8 | 149 | 0.025 |
| 27 | 80 | Top: 20 gsm, PET and PA ultrafine fibers Bottom: 60 gsm viscose | 670 | 7.0% | 94.3 | 150 | |

Ultrafine fiber*: from splittable PET/PA fiber

Aperture diameter*: Hydraulic diameter of aperture

Example 3: Absorbent Articles

Diaper samples 1-27 were fabricated using Pampers Hajimeteno Hadaeno Ichiban, size L (Procter and Gamble Japan K.K. Japan), and nonwoven prepared in Example 1 as AQS disposed between topsheets and absorbent cores. Firstly, a topsheet and an AQS layer disposed the topsheet and an absorbent core were carefully removed from a Pampers Hajimeteno Hadaeno Ichiban diaper by using cold spray agent. Then, a 22 gsm hydrophilic air-through non-woven (Z63 from Xiamen Yanjan New Material Co. Ltd, China) made from 1.2 denier hydrophilic PE/PET bico fibers as topsheet and each nonwoven prepared in Example 1 as ADS material were loosely laminated on the remaining diaper using 1 gsm spiral adhesive so that the topsheet and the ADS were connected to each other and to the remaining diaper and could be easily separated after tests.

Example 4: Absorbent Article Characteristics

Diaper samples produced in Example 3 were analyzed regarding total acquisition time and liquid in topsheet according to Fluid Acquisition Test and Liquid in Topsheet Test described in the MEASUREMENT section above. Results are summarized in Table 2.

TABLE 2

| Diaper | Nonwoven as ADS | Total acquisition Time (Sec) | Liquid in Topsheet (mg) |
|---|---|---|---|
| 1 | 1 | 699 | 102.2 |
| 2 | 2 | 759 | 139.8 |
| 3 | 3 | 582 | 212 |
| 4 | 4 | 570 | 247 |
| 5 | 5 | 327 | 119 |
| 6 | 6 | 286 | 133 |
| 7 | 7 | 287 | 133 |
| 8 | 8 | 315 | 238 |
| 9 | 9 | 302 | 122 |
| 10 | 10 | 281 | 105 |
| 11 | 11 | 233 | 116 |
| 12 | 12 | 359 | 523 |
| 13 | 13 | 211 | 388 |
| 14 | 14 | 474 | 109.9 |
| 15 | 15 | 287 | 374 |
| 16 | 16 | 534 | 414 |
| 17 | 17 | 293 | 451 |
| 18 | 18 | 560 | 270.4 |
| 19 | 19 | 555 | 266.3 |
| 20 | 20 | 561 | 280 |
| 21 | 21 | 493 | 369 |
| 22 | 22 | 306 | 606.1 |
| 23 | 23 | 255 | 624.5 |
| 24 | 24 | 262 | 661 |
| 25 | 25 | 240 | 492 |
| 26 | 26 | 326 | 308 |
| 27 | 27 | 310 | 537 |

Examples/Combinations

1. An absorbent article comprising:
   a liquid pervious topsheet,
   a liquid impervious backsheet,
   an absorbent core disposed between the topsheet and the backsheet, and
   an intermediate layer disposed between the topsheet and the absorbent core, the intermediate layer comprising a nonwoven, wherein the nonwoven comprises
i) a plurality of apertures,
ii) absorbent fibers, and
iii) ultrafine fibers of about 3% to about 35% by weight of the nonwoven, and
wherein at least most of the plurality of apertures have a hydraulic diameter in the range of about 600 μm to about 4500 μm.

2. An absorbent article comprising:
   a liquid pervious topsheet,
   a liquid impervious backsheet,
   an absorbent core disposed between the topsheet and the backsheet, and
   an intermediate layer disposed between the topsheet and the absorbent core, the intermediate layer comprising a nonwoven,
   wherein the nonwoven comprises a plurality of apertures, absorbent fibers, and ultrafine fibers,
   wherein the absorbent fibers are staple fibers having a fiber length no less than about 30 mm, and
   wherein the nonwoven has an air permeability no less than about 110 m³/m²/min as measured by Air Perme-ability Test disclosed herein, and a wicking rate no less than about 120 mm @ 300 s as measured by Wicking Rate Test disclosed herein.

3. An absorbent article comprising:
   a liquid pervious topsheet,
   a liquid impervious backsheet,
   an absorbent core disposed between the topsheet and the backsheet, and
   an intermediate layer disposed between the topsheet and the absorbent core, the intermediate layer comprising a nonwoven,
   wherein the nonwoven comprises a plurality of apertures, absorbent fibers, and ultrafine fibers,
   wherein the nonwoven has a fiber mixing extent of no less than about 0.040 as measured by Fiber Mixing Extent Test disclosed herein.

4. The absorbent article any of the preceding paragraphs, wherein the absorbent fibers are cellulose-based fibers.

5. The absorbent article according to any of the preceding paragraphs, wherein the nonwoven is a spunlace nonwo-ven.

6. The absorbent article according to any of the preceding paragraphs, wherein the topsheet comprises cellulose-based fibers.

7. The absorbent article according to any of the preceding paragraphs, wherein the nonwoven has a basis weight no less than about 45 gsm.

8. The absorbent article according to paragraph 1, wherein the nonwoven has an air permeability no less than about 110 m³/m²/min as measured by the Air Permeability Test.

9. The absorbent article according to paragraph 1 or 8, wherein the nonwoven has a wicking rate no less than about 120 mm @ 300 s as measured by the Wicking Rate Test.

10. The absorbent article of paragraph 1 or 2, wherein the nonwoven has a fiber mixing extent of no less than about 0.040 as measured by the Fiber Mixing Extent Test.

11. The absorbent article according to any of the preceding paragraphs, wherein the ultrafine fibers have a diameter no greater than about 2 μm.

12. A nonwoven comprising a plurality of apertures, the nonwoven comprises absorbent fibers, and ultrafine fibers of about 3% to about 35% of by weight of the nonwoven, wherein at least most of the apertures have a hydraulic diameter in the range of about 600 μm to about 4500 μm.

13. A nonwoven comprising a plurality of apertures, the nonwoven comprising absorbent fibers, and ultrafine fibers, wherein the absorbent fibers are staple fibers having a fiber length no less than about 30 mm, and wherein the nonwoven has an air permeability no less than about 100 m³/m²/min as measured by Air Permeability Test, and a wicking rate no less than about 120 mm @ 300 s as measured by Wicking Rate Test.

14. A nonwoven comprising a plurality of apertures, the nonwoven comprising absorbent fibers, and ultrafine fibers, wherein the nonwoven comprises a plurality of apertures, absorbent fibers, and ultrafine fibers, wherein the nonwoven has a fiber mixing extent of no less than about 0.040 as measured by Fiber Mixing Extent Test.

15. The nonwoven according to any of paragraphs 12-14, wherein the absorbent fibers are cellulose-based fibers.

16. The nonwoven according to any of paragraphs 12-15, wherein the nonwoven is a spunlace nonwoven.

17. The nonwoven of paragraph 12 or 13, wherein the nonwoven has a fiber mixing extent of no less than about 0.040 as measured by Fiber Mixing Extent Test.

18. The nonwoven according to paragraph 12, wherein the nonwoven has an air permeability no less than about 110 m³/m²/min as measured by Air Permeability Test.

19. The nonwoven according to paragraph 12 or 18, wherein the nonwoven has a wicking rate no less than about 120 mm @ 300 s as measured by Wicking Rate Test.

20. The nonwoven according to any of paragraphs 12-19, wherein the ultrafine fibers have a diameter no greater than about 2 μm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a liquid pervious topsheet;
a liquid impervious backsheet;
an absorbent core disposed between the topsheet and the backsheet; and
an intermediate layer disposed between the topsheet and the absorbent core, the intermediate layer comprising a nonwoven;
wherein the nonwoven comprises:
a plurality of apertures;
absorbent fibers;
hydrophobic ultrafine fibers of about 3% to about 35% by weight of the nonwoven;
wherein the absorbent fibers are entangled with the hydrophobic ultrafine fibers; and
wherein the hydrophobic ultrafine fibers have a diameter no greater than about 2 μm; and
wherein at least most of the plurality of apertures have a hydraulic diameter in the range of about 600 μm to about 4500 μm.

2. The absorbent article of claim 1, wherein the absorbent fibers are cellulose-based fibers.

3. The absorbent article of claim 2, wherein the nonwoven has a fiber mixing extent of no less than about 0.040 as measured by the Fiber Mixing Extent Test.

4. The absorbent article of claim 1, wherein the nonwoven is a spunlace nonwoven.

5. The absorbent article of claim 1, wherein the topsheet comprises cellulose-based fibers.

6. The absorbent article of claim 1, wherein the nonwoven has a basis weight no less than about 45 gsm.

7. The absorbent article of claim 1, wherein the nonwoven has an air permeability no less than about 110 m³/m²/min as measured by the Air Permeability Test.

8. The absorbent article of claim 1, wherein the nonwoven has a wicking rate no less than about 120 mm @ 300 s as measured by the Wicking Rate Test.

9. The absorbent article of claim 1, wherein the absorbent fibers are staple fibers having a fiber length no less than about 30 mm.

10. An absorbent article comprising:
a liquid pervious topsheet;
a liquid impervious backsheet;
an absorbent core disposed between the topsheet and the backsheet; and
an intermediate layer disposed between the topsheet and the absorbent core, the intermediate layer comprising a nonwoven;
wherein the nonwoven comprises a plurality of apertures, absorbent fibers, and hydrophobic ultrafine fibers;
wherein the hydrophobic ultrafine fibers have a diameter no greater than about 2 μm;
wherein the hydrophobic ultrafine fibers are split conjugate fibers;
wherein the split conjugate fibers comprise two components divided into two or more segments arranged in a circumferentially alternating pattern or in a layered pattern;
wherein the absorbent fibers are staple fibers having a fiber length no less than about 30 mm; and
wherein the nonwoven has an air permeability no less than about 110 m³/m²/min as measured by the Air Permeability Test, and a wicking rate no less than about 120 mm @ 300 s as measured by the Wicking Rate Test.

11. The absorbent article of claim 10, wherein the absorbent fibers are cellulose-based fibers.

12. The absorbent article of claim 10, wherein the nonwoven is a spunlace nonwoven.

13. The absorbent article of claim 10, wherein the topsheet comprises cellulose-based fibers.

14. The absorbent article of claim 10, wherein the nonwoven has a basis weight no less than about 45 gsm.

15. The absorbent article of claim 10, wherein the nonwoven has a fiber mixing extent of no less than about 0.040 as measured by Fiber Mixing Extent Test.

16. An absorbent article comprising:

a liquid pervious topsheet;

a liquid impervious backsheet;

an absorbent core disposed between the topsheet and the backsheet; and an intermediate layer disposed between the topsheet and the absorbent core, the intermediate layer comprising a nonwoven;

wherein the nonwoven comprises a plurality of apertures, absorbent fibers, and hydrophobic ultrafine fibers;

wherein the hydrophobic ultrafine fibers have a diameter no greater than about 2 $\mu$m;

wherein the absorbent fibers are entangled with the hydrophobic ultrafine fibers;

wherein the hydrophobic ultrafine fibers are split conjugate fibers;

wherein the split conjugate fibers comprise two components divided into two or more segments arranged in a circumferentially alternating pattern or in a layered pattern; and wherein the nonwoven has a fiber mixing extent of no less than about 0.040 as measured by Fiber Mixing Extent Test disclosed herein.

17. The absorbent article of claim 16, wherein the nonwoven has a basis weight no less than about 45 gsm.

18. The absorbent article of claim 17, wherein the absorbent fibers are staple fibers having a fiber length no less than about 30 mm, wherein the nonwoven has an air permeability no less than about 110 $m^3/m^2$/min as measured by Air Permeability Test, and a wicking rate no less than about 120 mm @ 300 s as measured by Wicking Rate Test.

\* \* \* \* \*